United States Patent
Kumei et al.

(10) Patent No.: US 7,828,721 B2
(45) Date of Patent: Nov. 9, 2010

(54) ELECTRONIC ENDOSCOPE

(75) Inventors: Kazuhiro Kumei, Tachikawa (JP); Takayuki Kato, Aizuwakamatsu (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 557 days.

(21) Appl. No.: 11/593,427

(22) Filed: Nov. 6, 2006

(65) Prior Publication Data

US 2007/0055104 A1 Mar. 8, 2007

Related U.S. Application Data

(63) Continuation of application No. PCT/JP2005/008800, filed on May 13, 2005.

(30) Foreign Application Priority Data

| May 14, 2004 | (JP) | ............................ 2004-145697 |
| Apr. 5, 2005 | (JP) | ............................ 2005-109094 |

(51) Int. Cl.
    *A61B 1/04* (2006.01)
(52) U.S. Cl. ....................... 600/109; 600/160; 600/176; 348/65
(58) Field of Classification Search ................ 600/104, 600/109, 118, 160, 167–168, 473, 475–476; 348/65, 68, 69
See application file for complete search history.

(56) References Cited

U.S. PATENT DOCUMENTS

| 6,254,531 B1 * | 7/2001 | Higuchi et al. .............. 600/178 |
| 6,824,509 B2 * | 11/2004 | Yamaya et al. .............. 600/106 |
| 7,537,561 B2 * | 5/2009 | Yamaya et al. .............. 600/106 |
| 2003/0191368 A1 * | 10/2003 | Wang et al. ................. 600/160 |
| 2003/0211405 A1 * | 11/2003 | Venkataraman ................ 430/7 |

FOREIGN PATENT DOCUMENTS

| JP | 01-234810 | 9/1989 |
| JP | 02-181111 | 7/1990 |
| JP | 07-088078 | 4/1995 |
| JP | 11-318819 | 11/1999 |
| JP | 2000-116598 | 4/2000 |
| JP | 2000-152913 | 6/2000 |
| JP | 2000152913 A * | 6/2000 |
| JP | 2000-330019 | 11/2000 |
| JP | 2005169009 A * | 6/2005 |

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

An insertion unit has a channel through which a treatment tool can be inserted. A distal end of the insertion unit has a single-focus objective optical system or a focal-point-variable objective optical system to focus the optical image on a light receiving surface of an image capturing element. At a short object distance from the distal end, an image signal with a sufficient resolution is obtained from the image capturing element. In this state, a treatment tool projected by a reduced amount from a distal end opening of the channel is captured on a light receiving surface of the image capturing element. A required resolution is also provided for a far side.

8 Claims, 18 Drawing Sheets

UPSIDE

DOWNSIDE

ELECTRONIC ENDOSCOPE

CROSS REFERENCE TO RELATED APPLICATION

This application is a continuation application of PCT/JP2005/008800 filed on May 13, 2005 and claims the benefit of Japanese Applications No. 2004-145697 filed in Japan on May 14, 2004 and No. 2005-109094 filed in Japan on Apr. 5, 2005, the entire contents of each of which are incorporated herein by their reference.

BACKGROUND OF THE INVENTION

1. Field of the Invention

The present invention relates to an electronic endoscope which comprises a solid image capturing element and which can be used with various treatment tools.

2. Description of the Related Art

As is well-known, endoscopes enable, for example, the interior of a living organism, which is not directly visible, to be observed and have been widely used for diagnosis and treatment mainly in medical fields. Further, electronic endoscopes have been prevailing which convert a subject image into an electric signal using a solid image capturing element such as a CCD so that the image can be observed via a monitor. In recent years, the following have also been spreading: electronic endoscopes that employ a zoom optical system in order to closely observe a subject and high-resolution endoscopes that use a multi-pixel solid image capturing element.

The former electronic endoscope employing a zoom optical system cannot adopt a complicated configuration owing to a limitation on the increased size of configuration of a distal end. Accordingly, resizing zoom optical systems are commonly used which move one lens group to vary the view angle.

Such a resizing zoom optical system as shown in Japanese Patent Laid-Open No. 2000-330019 is composed of a first lens group 10 having a negative refractive power, a brightness aperture S, a second lens group 20 having a positive refractive power, and a third lens group 30 having a negative refractive power; these groups are arranged in this order from an object as shown in FIG. 1 of this publication. This system is characterized in that for resizing, the second lens group 20 moves to two different points on an optical axis which do not vary an inter-object-image distance with the first lens group 10 and third lens group 30 immobilized. G denotes filters.

SUMMARY OF THE INVENTION

The present invention provides an electronic endoscope using a single-focus objective optical system comprising:
an insertion unit that is inserted into a subject;
a channel formed in the insertion unit and through which a treatment tool can be inserted; and
a single-focus objective optical system provided at a distal end of the insertion unit to form an optical image of the subject;
an image capturing element having a light receiving surface placed at a position where the objective optical system forms an image, to execute a photoelectric conversion on the optical image formed on the light receiving surface,
wherein if an image of a subject comprising a black band and a white band which have the same width is captured via the objective optical system and a brightness signal is generated from the resulting image signal and when a maximum value of a brightness signal for the white subject is defined as Imax, a minimum value of a brightness signal for the black subject is defined as Imin, and a contrast I is defined by I=(Imax−Imin)/(Imax+Imin),
when an image of a subject comprising a 0.5-mm pitch black and white band pair is captured at a distance of 50 mm from the distal end of the insertion unit, an image signal is output such that the contrast I defined above is at least almost 10%, and
at an object distance at which when an image of a subject comprising a 35-μm pitch black and white band pair is captured, an image signal is output such that the contrast I defined as described above is at least almost 10%, an image of vicinity of the distal end of the treatment tool projected from a distal end opening in the channel is formed on the light receiving surface of the image capturing element.

The present invention provides an electronic endoscope using a focal-position-varying objective optical system comprising:
an objective optical system provided in an insertion unit that is inserted into a subject;
an image capturing element comprising a predetermined number of pixels in which the objective optical system forms an optical image of the subject;
a lens moving unit that, when on the basis of a bright signal generated from an image signal resulting from image capturing of a subject comprising a black band and a white band which have the same width, a maximum value of a brightness signal for the white subject is defined as Imax, a minimum value of a brightness signal for the black subject is defined as Imin, and a contrast I is defined by I=(Imax−Imin)/(Imax+Imin), moves at least some of the lenses constituting the objective optical system to vary the focal distance of the objective optical system so that the depth of field has an overlapping part, in order to capture the subject located at a predetermined distance from the distal end of the insertion unit, at a contrast I of at least a predetermined value on a near point side of the objective optical system; and
a channel through which the treatment tool can be inserted and which is formed to be opened so as to locate the distal end of the treatment tool projected by a predetermined distance, within a view angle of the objective optical system when the lens moving unit sets focal distance on the near point side.

DETAILED DESCRIPTION OF THE PREFERRED EMBODIMENT(S)

Embodiments of the present invention will be described below with reference to the drawings.

Embodiment 1

Embodiment 1 of the present invention will be described with reference to FIGS. 1 to 6.

Figure 1:
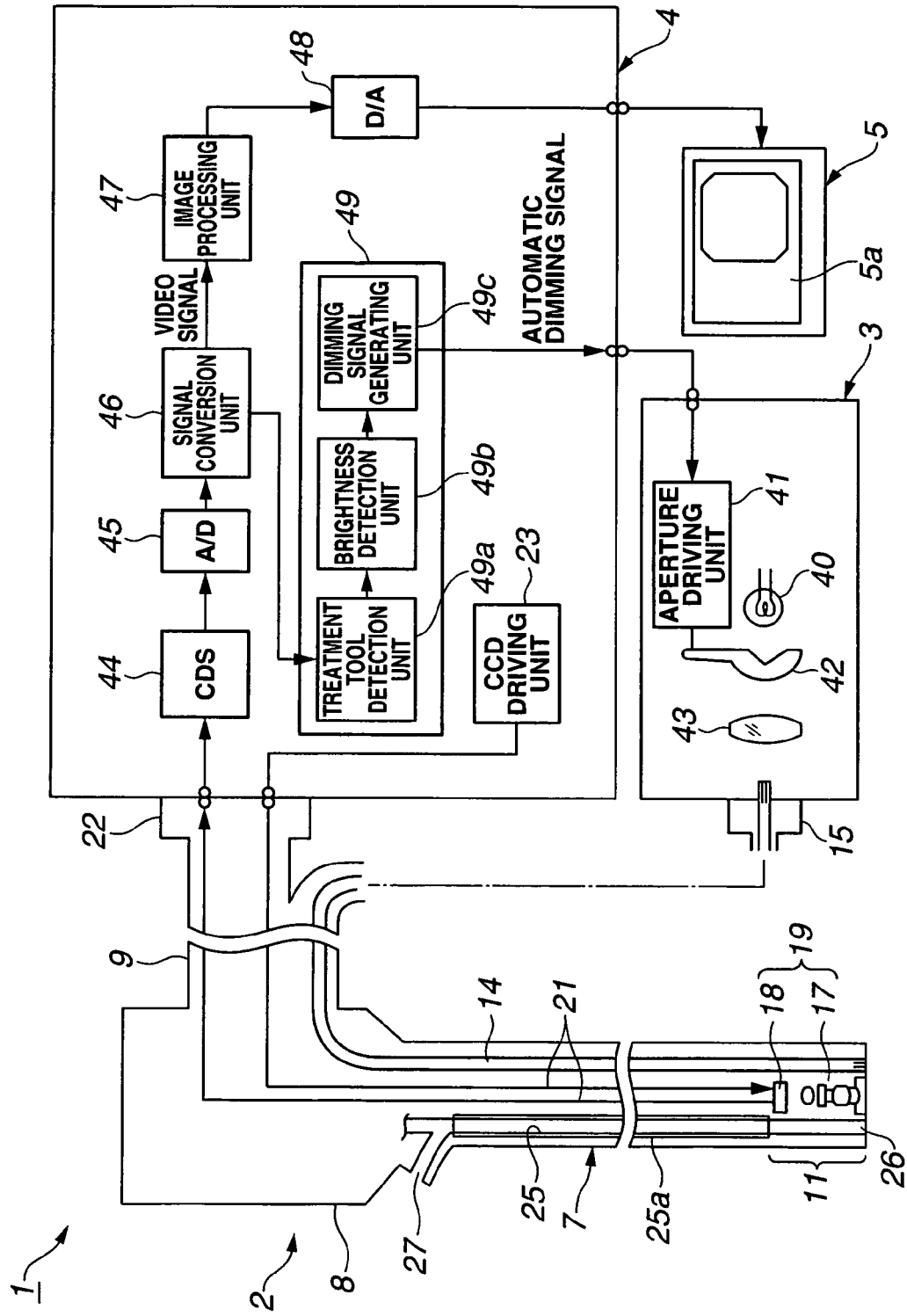
FIG. 1 is a diagram showing the general configuration of an endoscope system comprising Embodiment 1 of the present invention.

As shown in FIG. 1, an electronic endoscope system 1 is composed of an electronic endoscope 2 according to Embodiment 1, a light source device 3 that serves as a light source to supply illumination light for the electronic endoscope 2, an image processing device (signal processing device) 4 incorporated in the electronic endoscope to process signals for image capturing means, and a monitor 5 which supports a high vision TV (hereinafter simply referred to as HDTV) to which standard video signals output by the image processing device 4 are input, to display endoscope images.

The electronic endoscope 2 in the present embodiment has an insertion unit 7 that is inserted into a subject, a manipulation unit 8 provided at a trailing end of the insertion unit 7 that is operated by a user, and a cable unit 9 extended from the manipulation unit 8.

The insertion unit 7 has a rigid distal end portion 11 at its tip which is provided with an image capturing unit and the like described below.

A light guide 14 is inserted through the insertion unit 7 to transmit illumination light. A trailing end of the light guide 14 leads through a cable unit 9 to a light guide connector 15 provided at an end of the cable unit 9. Connection of the light guide connector 15 to the light source device 3 allows the light source device 3 to supply illumination light to a trailing end surface of the light guide 14.

Illumination light supplied by the light source device 3 is transmitted via the light guide 14. The light is emitted forward from a distal end surface fixed to the distal end portion 11, through illumination lenses 16a and 16b (see FIG. 3) attached to an illumination window opposite the distal end surface. The light thus illuminates a subject such as a diseased site in the celom or the like.

The distal end portion 11 is provided with an observation window (or an image capturing window) adjacent to the illumination window. An image capturing unit 19 is placed in the image capturing window; the image capturing unit comprises an objective lens system (or objective optical system) 17 that forms an optical image of the illuminated subject, and for example, a charge coupled device (hereinafter simply referred to as a CCD) 18 which serves as an image capturing element and which has a light receiving surface (or photoelectrical converting surface) placed at the position where the objective lens system 17 forms an image.

One end of the signal cable 21 is connected to the image capturing unit 19. The signal cable 21 inserted through the insertion unit 7 is further inserted through the cable unit 9. The other end of the signal cable 21 is connected to a signal connector 22 located at a trailing end of the cable unit 9.

Connection of the signal connector 22 to the image processing device 4 allows the CCD 18 to be driven in accordance with a CCD driving signal from a CCD driving unit 23 of the image processing device 4. The CCD 18 then outputs a photoelectrically converted image signal (image capturing signal).

The image capturing signal is processed in the image processing device 4. An endoscope image is displayed on the monitor 5.

A channel 25 is formed in the insertion unit 7 so that various treatment tools can be inserted through the channel 25. The channel 25 comprises a channel distal end opening (also referred to as a distal end opening or forceps port) 26 formed in the distal end portion 11, a treatment tool insertion port 27 located near a front end of the manipulation unit 8, and a channel tube 25a that connects the distal end opening 26 and the treatment tool insertion port 27 together.

Insertion of a treatment tool 28 through the treatment tool insertion port 27 allows a distal end of the treatment tool 28 to be projected from the distal end opening 26. The diseased tissue can be collected or excised using the distal end of the treatment tool 28.

Further, the present embodiment allows a subject such as a diseased tissue which is to be examined or treated and the distal end of the treatment tool 28 projected from the distal end opening 26 to come into the view of the image capturing unit 19 with a reduced amount of projection. This enables the distal end of the projected treatment tool 28 to be displayed on a display surface of the monitor 5. An operator can smoothly execute treatment or the like.

In the present embodiment, the CCD 18 is based on a mosaic color filter scheme and comprises a complementary-color mosaic color filter. The CCD 18 has a pixel pitch of 2.5 μm and uses 810 thousand pixels that are effective for monitor display. The CCD 18 also has a maximum image height of 1.3 mm on the CCD light receiving surface.

The image capturing unit 19 uses a single-focus objective lens system 17 having a maximum angle of view of 138°. The objective lens system 17 is set to have an Fno (F number) of 10.0 so as not to exceed a light diffraction limit. Further, the focus is adjusted so as to obtain the maximum resolution at an object distance of 4.2 mm.

Lens data on the objective lens system 17 used in the present embodiment is shown below. Here, F1 denotes the focal distance of the objective lens system 17. Ra denotes the radius of curvature of a lens. Da denotes a surface interval. Ne denotes a refractive index for a mercury e line (wavelength: 546.07 nm). Vd denotes an Abbe number.

| F1 = 1.33785 mm | | | | |
|---|---|---|---|---|
| Surface No. | Ra | Da | Ne | Vd |
| 1 | ∞ | 0.40 | 1.77067 | 71.7 |
| 2 | 0.977 | 0.57 | | |
| 3 | ∞ | 0.40 | 1.52498 | 59.9 |
| 4 | ∞ | 0.84 | | |
| 5 | ∞ (aperture) | 0.03 | | |
| 6 | ∞ | 1.90 | 1.801078 | 40.9 |
| 7 | −2.192 | 0.10 | | |
| 8 | 3.168 | 1.68 | 1.51825 | 64.1 |
| 9 | −1.676 | 0.39 | 1.93429 | 18.9 |
| 10 | −5.048 | 0.10 | | |
| 11 | ∞ | 0.60 | 1.51965 | 75.0 |
| 12 | ∞ | 1.16 | | |
| 13 | ∞ | 1.00 | 1.51825 | 64.1 |
| 14 | ∞ | 0.03 | 1.5119 | 64.1 |
| 15 | ∞ | 1.00 | 1.61379 | 50.2 |
| 16 | ∞ | 0.00 | | |

Figure 2:
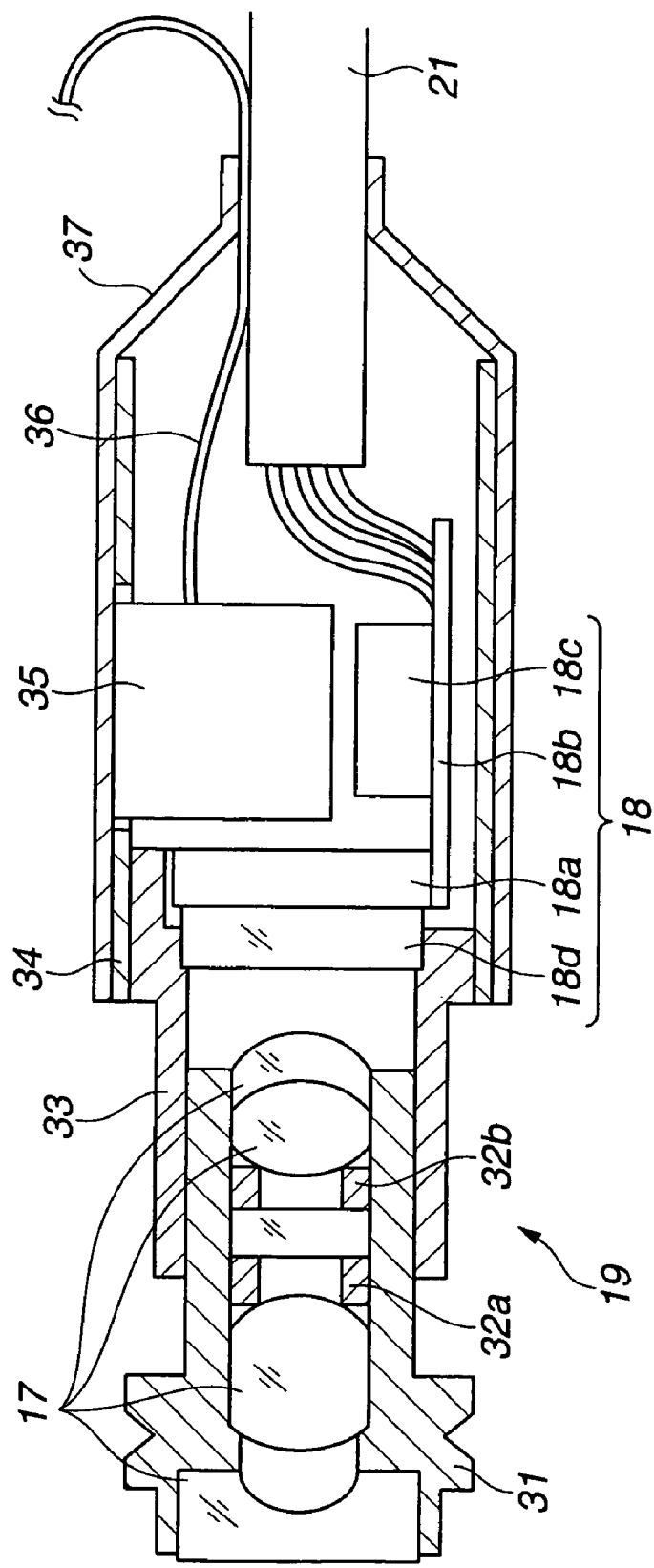
FIG. 2 is a sectional view of an image capturing unit in the electronic endoscope of Embodiment 1.

The configuration of the image capturing unit 19 will be described with reference to FIG. 2.

A plurality of lenses constituting the objective lens system 17 are fixedly held using a lens frame 31 and spacers 32a and 32b so as to be centered and to maintain the proper surface spacing. The CCD 18 is composed of a CCD chip 18a, a CCD substrate 18b, a CCD driving part 18c, and sealing glass 18d.

The CCD substrate 18b is electrically connected to the CCD chip 18a by wire bonding or the like and mechanically fixed with an adhesive or the like. A coupling capacitor and the CCD driving part 18c such as a current amplifying transistor are arranged on and soldered to the CCD substrate 18b. The sealing glass 18d is fixedly bonded to the light receiving surface of the CCD chip 18a with an optical adhesive or the like in order to protect the light receiving surface.

The lens frame 31 is fitted into a CCD frame 33 so as to be movable parallel to the optical axis of the objective lens system 17. The CCD 18 is fixedly bonded to the CCD frame 33 so that the optical axis of the objective lens system 17 is perpendicular to the light receiving surface of the CCD 18.

A land (not shown) is provided on the CCD substrate 18b so that a signal line in the signal cable 21 can be soldered to the land. The signal line in the signal cable 21 is soldered to the land. A CCD protect frame 34 is placed so as to protect an area from the CCD frame 33 through the CCD 18 to the connection of the signal cable 21 with the CCD substrate 18b.

The CCD protect frame 34 has a notch portion formed near the back surface of the CCD chip 18a. A thermally conductive heat radiation member 35 formed of, for example, an aluminum alloy or a copper alloy is placed so as to be inserted through the notch portion. A heat radiation cable 36 comprising a thermally conductive metal as a conductor is mechanically connected to the heat radiation member 35 with solder, an adhesive, or the like.

A sealing resin is filled into the CCD protect frame 34, and the periphery of CCD 18 is sealed with a thermally contractive tube 37. The heat radiation cable 36 is soldered to a member with a large thermal capacity, for example, the distal end portion 11 of the insertion unit 7. The signal cable 21 is formed by twisting a plurality of coaxial wires and a plurality of single wires together, winding a fluorine resin tape around the wires, further winding a copper wire around the tape as a bundle shield, further winding a fluorine resin tape around the wire, and covering the tape with a Teflon (registered trade mark) based sheath.

Figure 3:
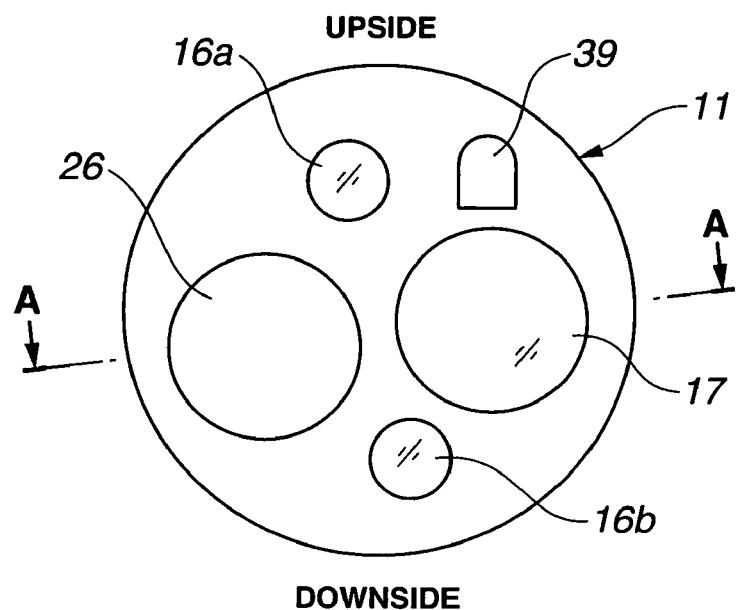
FIG. 3 is a diagram showing the appearance of the distal end surface of a distal end of an insertion unit in Embodiment 1 as viewed from the front.

As shown in FIG. 3, the image capturing unit 19, the channel distal end opening 26, an air and water supplying nozzle 39, and the illumination lenses 16a and 16b are disposed in the distal end portion 11 of the insertion unit 7; the image capturing unit 19 includes the objective lens system 17 having a distal end lens of outer diameter φ2.8 mm, the air and water supplying nozzle 39 feeds water or gas to the outer surface of the objective lens system 17 to remove contaminants, and the illumination lenses 16a and 16b are used to illuminate the subject with light transmitted (conducted) through the light guide 14 connected to the light source device 3.

The image capturing unit 19 is attached to the distal end portion 11 so that the up and down direction of a captured image of the subject displayed on the monitor 5 aligns with the up and down direction of the distal end portion 11 of the insertion unit 7 in FIG. 3. The channel tube 25a in the present embodiment is made of Teflon (registered trade mark) and has an inner diameter of 2.8 mm.

Figure 4:
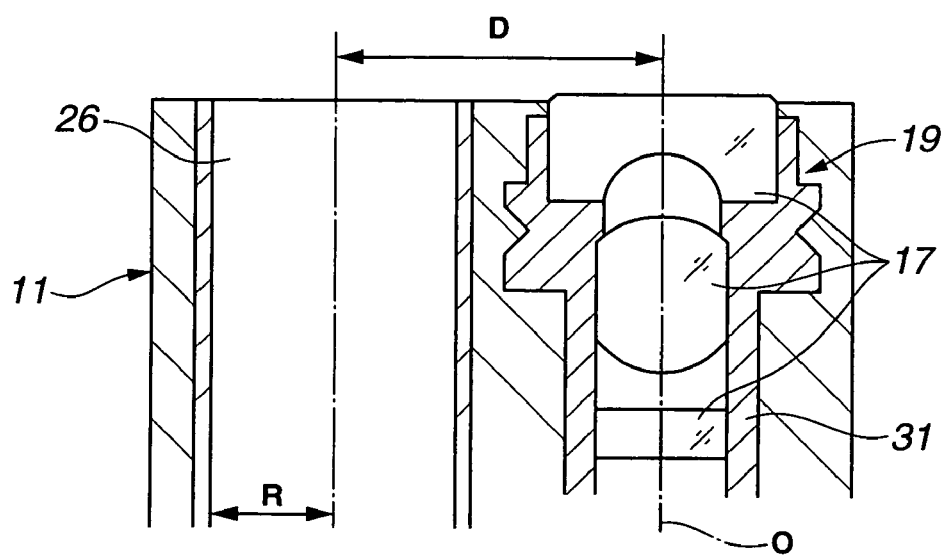
FIG. 4 is a schematic sectional view taken along line A-A in FIG. 3.

As shown in FIG. 4, the optical axis O of the objective lens system 17 is placed parallel to the distal end opening 26 (to which the distal end of the channel tube 25a is connected). In the present embodiment, the distance D between the center (optical axis O) of the objective lens system 17 and the center axis of the distal end opening 26 is set at 6 mm. Double the radius R of the distal end opening 26 is equal to the inner diameter of the channel tube 25a, 2.8 mm.

As shown in FIG. 1, the light source device 3 has a lamp 40. Illumination light from the lamp 40 has its light transmission amount adjusted by the opening of the aperture 42, driven by the aperture driving unit 41. The light then enters an incident end surface of the light guide 14 of the light guide connector 15 through a light condensing lens 43. The illumination light is then emitted from the distal end of the light guide 14 to the subject through the illumination lenses 16a and 16b as described above.

The light guide 14 branches to two portions inside the insertion unit 7. The illumination light is thus emitted from the illumination lenses 16a and 16b, arranged at the respective positions in the distal end portion 11 as shown in FIG. 3.

As shown in FIG. 1, the image processing device 4 has a CDS circuit 44 to which an image signal from the CCD 18 is input. The CDS circuit 44 extracts a signal component and an A/D converter 45 converts the signal component into a digital signal.

The resulting digital image signal from the A/D converter 45 is input to a signal conversion unit 46 that generates a video signal comprising a brightness signal and a chrominance signal. A video signal generated by the signal conversion unit 46 is input to an image processing unit 47 that executes various image processes such as γ correction. An output signal from the image processing unit 47 is input to a D/A converter 48. The signal is thus converted into a video signal compatible with an analog HDTV scheme, which is then output to the monitor 5.

Further, a brightness signal from the signal conversion unit 46 is input to an automatic dimming unit 49, which then generates an automatic dimming signal. The automatic dimming signal is input to the aperture driving unit 41 of the light source device 3 to automatically adjust the numerical aperture of the aperture 42.

The automatic dimming unit 49 contains a treatment tool detection unit 49a that detects that a treatment tool has come into the view of the image capturing unit 19 (in other words, an image of the treatment tool is formed on the light receiving surface of the CCD 18), on the basis of, for example, the quantity of light reflected by the treatment tool or its color.

Further, the automatic dimming unit 49 has a brightness detection unit 49b that detects brightness to be adjusted in an output signal from the treatment tool detection unit 49a and a dimming signal generating unit 49c that generates an automatic dimming signal from an output signal from the brightness detection unit 49b.

If the treatment tool detection unit 49a detects a treatment tool, the brightness detection unit 49b detects the peak brightness (light quantity) of vicinity of the area in which an image of the treatment tool is formed and the average brightness (light quantity) of the vicinity.

Further, if the treatment tool detection unit 49a does not detect any treatment tool, the brightness detection unit 49b detects the peak brightness and average brightness of the entire screen.

Furthermore, the dimming signal generating unit 49c generates an automatic dimming signal that adjusts the illumination light quantity of the light source device 3 so as to obtain a signal with a proper brightness, on the basis of signals for the peak brightness and average brightness from the brightness detection unit 49b. The dimming signal generating unit 49b then outputs the automatic dimming signal to the aperture driving unit 41 of the light source device 3.

With the electronic endoscope 2 of the present embodiment, the image capturing unit 19, comprising the single-focus objective lens system 17, indicated by the above lens data, and the CCD 18, offers a resolution at which 35-μm pitch black and white subjects can be distinguished from one another, which is higher than a conventionally achievable resolution at which about 50-μm pitch black and white subjects to be distinguished from one another (the image capturing system 17 meets the corresponding condition). The image capturing unit 19 also offers a resolution required to observe a distant view, which is comparable to that in the prior art.

To output an image signal corresponding to this resolution, the CCD 18 of the image capturing unit 19 executes signal processing to generate a standard video signal for the image signal. If the video signal is displayed on the display surface of the monitor 5, the display image enables 35-μm pitch black and white subjects to be distinguished from one another.

The resolution required to observe the distant view side enables 0.5-mm pitch black and white subjects to be distinguished from one another at a distance of, for example, about 50 mm from the image capturing unit 19. This resolution is called a distant view resolution. Further, the resolution required to enable the 35-μm pitch black and white subjects to be distinguished from one another is called a proximity side close resolution.

Further, according to the present embodiment, the distal end of the treatment tool 28 comes into the view of the image capturing unit 19 at an object distance at which if the distal end of the treatment tool 28 inserted through the channel 25 is projected from the distal end opening 26, the resolution required to enable 35-μm pitch black and white subjects to be distinguished from one another is obtained.

Further, an image of the distal end of the treatment tool 28 projected only by a small amount is formed on the light receiving surface of the CCD 18. This enables the vicinity of distal end of the treatment tool 28 to be closely observed, allowing close treatments to be executed using the treatment tool 28.

Description will be given of effects of the present embodiment configured as described above.

As shown in FIG. 1, the light guide connector 15 of the electronic endoscope 2 is connected to the light source device 3. Further, the signal connector 22 is connected to the image processing device 4. Furthermore, the cable from the monitor 5 is connected to a picture output end of the image processing device 4 to allow endoscope examinations to be executed.

Then, a power supply switch (not shown) is turned on to supply illumination light from the light source device 3 to the light guide 14. The illumination light is emitted from the illumination lenses 16a and 16b via the light guide 14 so that the subject, which is to be subjected to image capturing by the image capturing unit 19, can be illuminated. Further, under these conditions, an image captured by the CCD 18 of the image capturing unit 19 is displayed on the monitor 5 via the image processing device 4.

Then, the insertion unit 7 of the electronic endoscope 2 is inserted into the patient's celom so that the subject in the site which is to be examined using the endoscope, such as a diseased site in the celom, can be observed using the distal end portion 11 of the insertion unit 7.

In this case, the objective lens system 17 of the image capturing unit 19, provided in the distal end portion 11, forms an optical image of the subject on the light receiving surface of the CCD 18. The image formed on the light receiving surface of the CCD 18 is photoelectrically converted into an image signal. The image signal is input to the CDS circuit 44 of the image processing device 4 via the signal cable 21 and signal connector 22. The image signal has a waveform containing reset noise or the like in addition to a signal component. The CDS circuit 44 extracts the signal component to generate a baseband signal.

An output signal from the CDS circuit 44 is input to the A/D converter 45, which then converts the image signal, which is an analog signal, into a digital signal. The image signal converted into the digital signal is further converted into a video signal by the signal conversion unit 46.

In this case, the present embodiment employs a complementary-color mosaic color filter as the CCD 18. Accordingly, the signal conversion unit 46 converts the image signal into a video signal such as a brightness signal that is the average of pixel signal outputs from adjacent four types of color filters or a color difference signal obtained from the differences among pixel signal outputs of specific colors.

This video signal has its contrast, color, display size, and the like adjusted by the image processing unit 47 so as to have suitable values for monitor display.

The D/A converter 48 converts the video signal into a signal which is compatible with the analog HDTV scheme and which can be displayed on the monitor 5. The monitor 5 displays the image of the subject (captured by the CCD 18) corresponding to the input HDTV-compatible video signal, on a monitor screen 5a.

Now, with reference to FIG. 6, description will be given of effects of the present embodiment exerted when the image capturing unit 19 captures an image of a subject comprising a 35-μm pitch black and white band pair.

Figure 6:
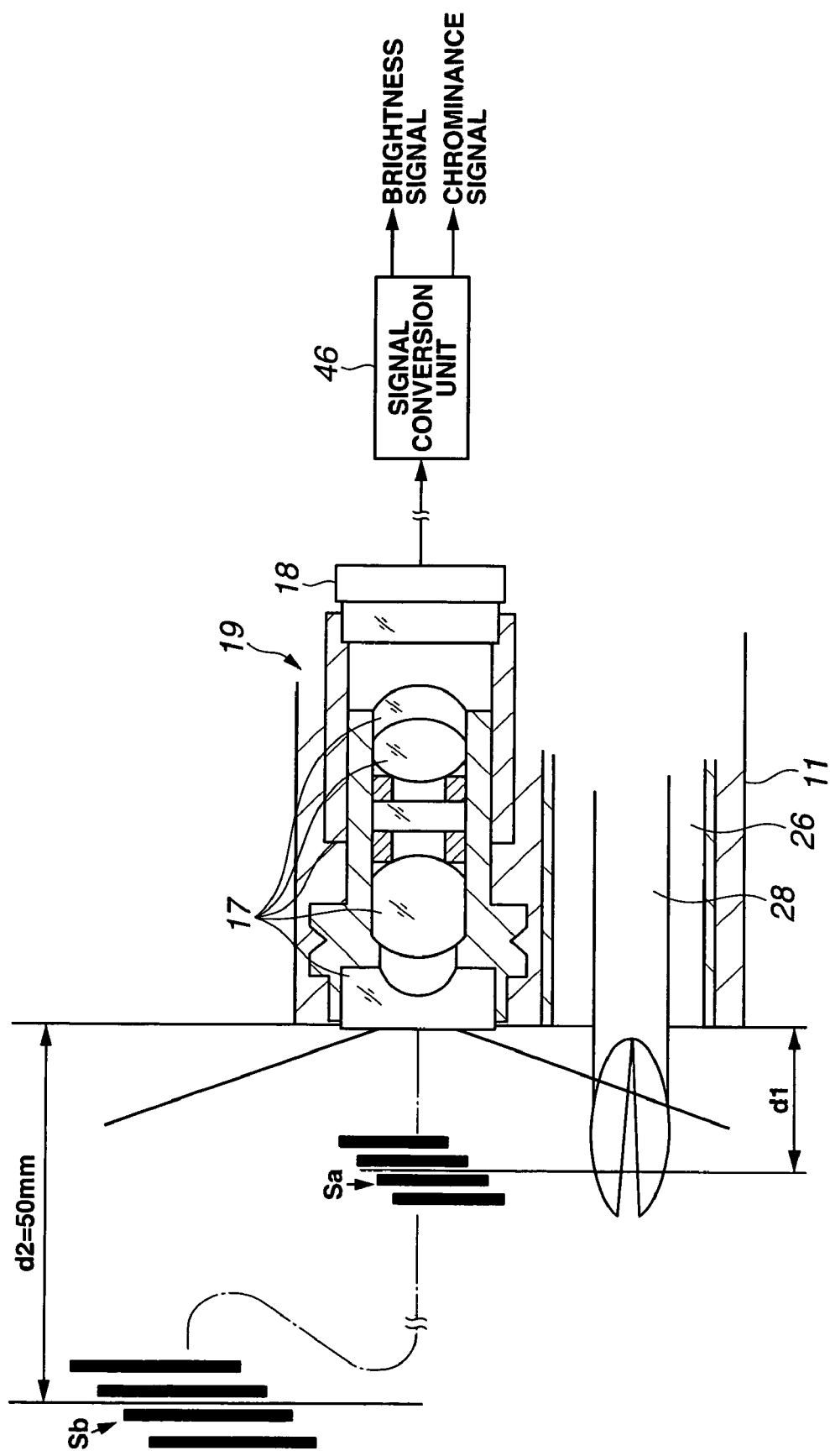
FIG. 6 is a diagram schematically illustrating the effects of Embodiment 1.

FIG. 6 is a schematic diagram showing that the insertion unit 7 of the electronic endoscope 2 of the present embodiment is inserted into the celom and that the image capturing unit 19, provided in the distal end portion 11, is used to capture an image of the treatment target site in the celom, while the treatment tool 28 is projected from the distal end opening 26 for treatment.

In this case, the conditions under which treatment can be easily executed include an appropriate resolution at which an image of the distant view can be captured (observed). Further, it is desirable to be able to closely observe the diseased site or the like to be treated and to closely observe the distal end of the treatment tool 28 projected from the distal end opening 26.

The present embodiment meets these conditions as described below. First, for clear description, the brightness contrast G is defined as described below.

When an image of a black band subject and a white band subject (stripes) which have the same width is formed on the light receiving surface of the CCD 18 via the objective lens system 17, the maximum value of brightness of the white subject is defined as Gmax, the minimum value of brightness of the black subject is defined as Gmin, and the brightness contract G is defined by G=(Gmax−Gmin)/(Gmax+Gmin).

If the brightness contrast G is thus defined, when the image capturing unit 19 configured as described above captures an image of black and white band subjects arranged at a pitch of 35 μm, at an object distance of 4.2 mm, at which the best resolution is obtained, the brightness contrast G of the black and white bands formed on the CCD light receiving surface is 14.5%.

For the image of the subject comprising the 35-μm pitch black and white band pair formed on the light receiving surface of the CCD 18 by the objective lens system 17, the difference between an image signal output from the pixel at which an image of the white band is formed and an image signal output from the pixel at which an image of the black band is formed is approximately 14.5%.

The image signal is input to the image processing unit 47 via the CDS circuit 44, A/D converter 45, and signal conversion unit 46. The signal is then subjected to, for example, a gamma process suitable for the monitor 5 or a low pass filter process for removing noise.

If the maximum value of a brightness signal obtained from the white subject is defined as Imax, the minimum value of a brightness signal obtained from the black subject is defined as Imin, and the contrast I is defined by I=(Imax−Imin)/(Imax+Imin), (when an image of the 35-μm pitch black and white band subjects is captured) the resulting signal is output with a contrast I of at least 10%. Thus, the image of the 35-μm pitch black and white bands captured by the image capturing unit 19 can be viewed as a black and white band pair on the monitor 5.

In FIG. 6, if an object distance of 4.2 mm, at which the best resolution is obtained, is defined as dI and the 35-μm pitch black and white bands (stripes) Sa are arranged at that position, a brightness signal forming a video signal output by, for example, the signal conversion unit 46 as a result of the photoelectric conversion by the CCD 18 has a contrast I of at least 10%. This enables the 35-μm pitch black and white band pair to be viewed on the monitor 5.

Further, when the 35-μm pitch black and white band pair can be viewed on the monitor 5, if the image capturing unit 19 is used to capture an image of a subject Sb placed at an object distance of 50 mm and comprising a 0.5-mm pitch black and white band pair, then an image of the black and white bands formed on the CCD light receiving surface has a contrast G of 25%.

Similarly, for an image of a subject comprising a 0.5-mm pitch black and white band pair formed on the light receiving surface of the CCD 18, the difference between an image signal output from the pixel at which an image of the white band is formed as a result of a photoelectric conversion and an image signal output from the pixel at which an image of the black band is formed as a result of a photoelectric conversion is about 25%. The image processing device 4 thus outputs the image on the monitor 5 so that the black and white bands have a contrast I of at least 10%. This enables the 0.5-mm pitch black and white band pair to be viewed on the monitor 5 as a black and white band pair; the 0.5-mm pitch black and white band pair is placed at a distance of 50 mm and an image of the pair has been captured by the image capturing unit 19.

FIG. 6 shows that a 0.5-mm pitch black and white band pair (stripes) Sb is placed at an object distance d2 of 50 mm. Also in this case, a brightness signal from the signal conversion unit 46 has a black and white contrast I of at least 10%. This enables the black and white band pair to be viewed on the monitor 5.

Figure 5:
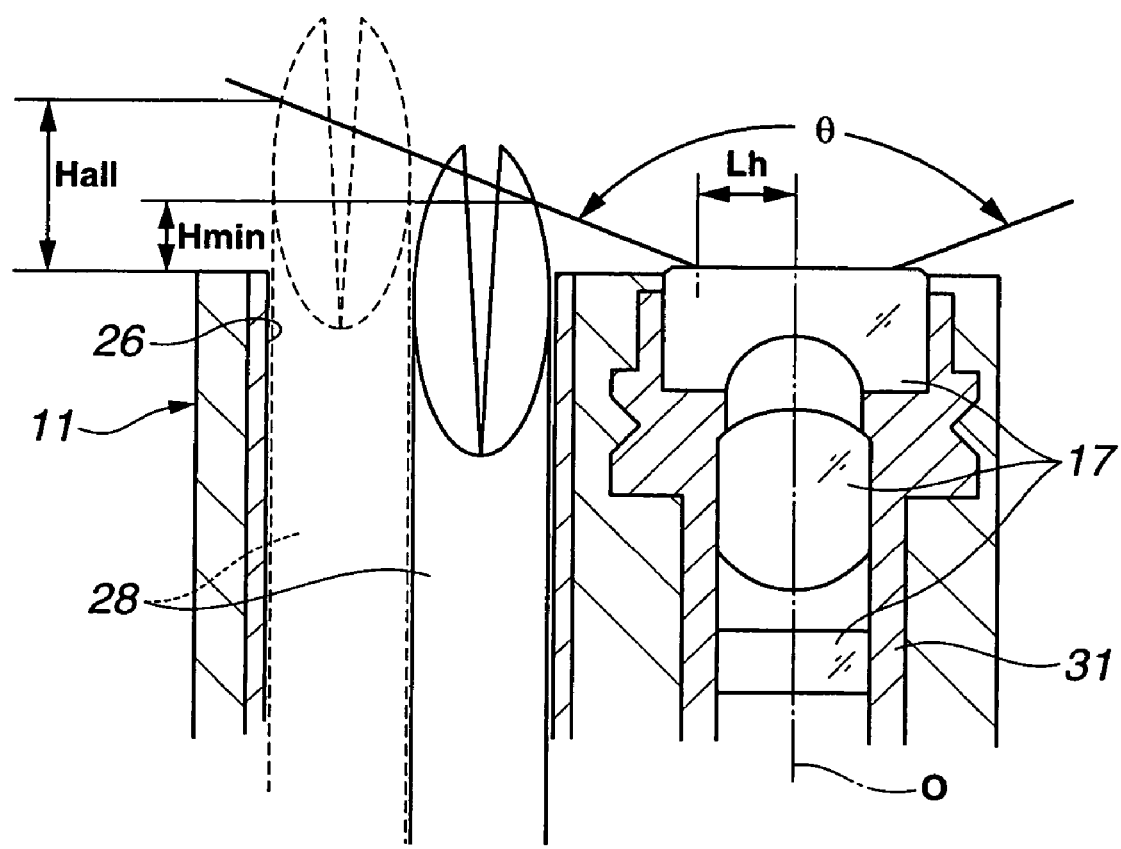
FIG. 5 is a schematic sectional view showing how a treatment tool inserted through a channel is projected from a distal end opening, and the like in FIG. 4.

Now, description will be given of insertion of a treatment tool through the channel 25 for treatment. A manipulator inserts a treatment tool to be used into the treatment tool insertion port 27, formed in the vicinity of the manipulation unit 8. The treatment tool inserted through the treatment tool insertion port 27 passes through the channel 25 in the channel tube 25a in the insertion unit 7. The treatment tool 28 is then guided to the distal end portion 11 of the insertion unit 7. As the manipulator further inserts the treatment tool 28 deeper, the distal end of the treatment tool 28 projects from the channel distal end opening 26 in the distal end portion 11. Description will be given of conditions for allowing the image capturing unit 19 to capture an image of the projecting treatment tool 28. If the treatment tool 28 projects from the distal end surface of distal end portion 11 of the insertion unit 7 by the minimum amount, that is, if the treatment tool 28 is shifted closest to the image capturing unit 19 as shown in FIG. 5, the minimum projection amount Hmin is derived from the light height Lh=1.2 mm on the distal end lens surface of the image capturing unit 19, the radius R=1.4 mm of the distal end opening 26, the angle of view θ=138° of the image capturing unit 19, and the distance D=6 mm between the optical axis O of the image capturing unit 19 and the center of the distal end opening 26 as shown in Equation 1.

$$H\text{min}=(D-Lh-R)\times\tan(90°-\theta/2)=1.38 \text{ mm} \quad \text{(Equation 1)}$$

On the other hand, if the treatment tool 28 is positioned at the largest distance from the image capturing unit 19, the condition for allowing the image capturing unit 19 to capture an image of the entire distal end of the treatment tool 28, that is, the amount Hall of projection of the treatment tool 28 from the distal end surface of distal end portion 11 of the insertion unit 7, is derived as shown in Equation 2.

$$H\text{all}=(D-Lh+R)\times\tan(90°-\theta/2)=2.45 \text{ mm} \quad \text{(Equation 2)}$$

As shown in Equations 1 and 2, the treatment tool 28 starts to come into the view of the image capturing unit 19 when the amount of projection of the distal end portion 11 from the distal end surface is at least 1.38 mm. When the distal end portion 11 is projected by 2.45 mm, almost the entire distal end of the treatment tool 28 comes into the view of the image capturing unit 19.

Thus, at an object distance of 4.2 mm, at which the image capturing unit 19 according to the present embodiment offers the best resolution, the distal end of the treatment tool 28 is ensured to come into the view of the image capturing unit 19. Consequently, the distal end can be viewed on the monitor 4.

FIG. 6 also shows that the treatment tool 28 projects from the distal end opening 26 of the channel. After the distal end of the treatment tool 28 comes into the view of the image capturing unit 19, projecting the treatment tool 28 further forward places the distal end at an object distance for the maximum resolution.

This enables the subject such as a diseased site which is to be treated using the treatment tool 28 to be closely observed. The distal end of the treatment tool 28 projecting to the vicinity of the subject can also be closely observed. This facilitates treatment. Further, under these conditions, the distant view resolution is provided for the distant view. This makes it possible to determine the status of a wide peripheral area of the site to be treated, allowing treatment to be executed more smoothly.

Now, an automatic dimming function according to the present embodiment will be described.

If the treatment tool 28 is not within the range of view of the image capturing unit 19, an automatic dimming unit 49 uses a brightness detection unit 49b to sense the brightness (specifically, the peak brightness or average brightness) of the entire screen and outputs the brightness to a dimming signal generating unit 49c. When the screen is dark, the dimming signal generating unit 49c outputs a control signal allowing the light source device 3 to increase the light quantity, specifically an automatic dimming signal. If the screen is too bright, the dimming signal generating unit 49c outputs an automatic dimming signal serving as a control signal that controls the light source device 3 so that the light quantity is reduced.

The automatic dimming signal allows the aperture driving unit 41 in the light source device 3 to drive the aperture 42 to adjust the quantity of illumination light exiting the lamp 40 and entering an incident end of the light guide 14 via the aperture 42. Now, description will be given of effects of automatic dimming in using the treatment tool 28 to collect tissues or excise a lesion site through endoscope examinations with the image capturing unit 19 in order to treat the subject such as a diseased site.

The treatment tool 28 is inserted through the channel 25 so as to project from the distal end surface via the distal end opening 26 of the distal end portion 11 of the insertion unit 7 through the distal end opening 26 in the distal end portion 11. This allows the treatment tool to come into the view of the image capturing unit 19.

In this case, the treatment tool detection unit 49a senses that the treatment tool 28 has come into view on the basis of, for example, the color of the treatment tool 28 or reflected light from the treatment tool 28. The treatment tool detection unit 4 senses the brightness on the basis of the peak or average brightness of a given area around the treatment tool 28. A dimming signal generating unit 49c outputs an automatic dimming signal serving as a control signal such that the quantity of light from the light source device 3 is reduced if the vicinity of the treatment tool 28 is too bright and is increased if the vicinity of the treatment tool 28 is too dark.

The automatic dimming signal allows the aperture driving unit 41 in the light source device 3 to drive the aperture 42 to adjust the quantity of illumination light exiting the lamp 40 and entering the trailing end of the light guide 14 via the aperture 42 from a lump 40. The automatic dimming signal enables automatic dimming such that the vicinity of the area in which the treatment tool 28 comes into the view of the image capturing unit 19 has a brightness suitable for observations.

A method for adjusting the illumination light quantity, besides aperture control by the aperture driving unit 42, is to provide a control unit that controls power (current value, voltage value, or the like) supplied to the light source to adjust the power and thus the illumination light quantity. Alternatively, a light emission diode (LED) serving as a light source may be provided at the distal end of the insertion unit 7 so that a current supplied to the light emission diode can be adjusted on the basis of detection by a brightness detection unit 49b to control the light emission quantity (illumination light quantity).

Now, description will be given of effects of the heat radiation member 35 and heat radiation cable 36, arranged in the image capturing unit 19.

Driving the CCD 18 causes the CCD chip 18a and the CCD driving part 18c such as a current amplifier to generate heat. In general, driving frequency and power consumption increase consistently with the number of pixels. This causes the CCD chip 18a to generate heat. Since the heat radiation member 35 is placed adjacent to the CCD chip 18a and CCD substrate 18b, heat from the CCD 18 is transferred to the heat radiation member 35. The heat is subsequently transferred to the heat radiation cable 36. Moreover, the heat is transferred to the distal end member of the insertion unit 7, to which the heat radiation cable 36 is connected. The heat generated by the CCD 18 is thus released to prevent the CCD chip 18a from generating excessive heat.

Further, the signal cable 21 comprises a tape wound between a bundle shield and a sheath. Accordingly, when for example, the signal cable 21 is subjected to twisting mechanical stress, the tape between the bundle shield and the sheath reduces the friction between the bundle shield and the sheath resulting from a difference in twisting between the sheath and the bundle shield as well as the tensile force of the sheath exerted on the bundle shield. This is effective in improving twist resistance.

The present embodiment exerts the effects described below.

The present embodiment adopts the single-focus optical system as an objective optical system constituting the image capturing unit 19. This enables the structure of the image capturing unit 19 to be simplified compared to that of a resizing optical system or a variable-focus optical system.

The resolution of an image capturing unit adopting a single-focus optical system used in conventional electronic endoscopes is at a level at which a subject comprising a black and white band pair with pitch of about 50 μm can be recognized. In contrast, as previously described, the image capturing unit 19 according to the present embodiment enables the recognition of a subject comprising a black and white band pair with a pitch of 35 μm, which corresponds to a higher resolution.

Further, at a distance at which the maximum resolution of the image capturing unit 19 is obtained, the distal end of the treatment tool 28 projecting from the distal end opening 26 of the channel 25 can be viewed on the monitor 5. This enables such an operation as executes treatment while making close observations; such an operation is difficult to perform with a conventional endoscope using a zoom optical system. For example, the present embodiment is effective in enabling treatment to be executed using the treatment tool 28 while closely observing a subject, for example, a pit pattern in the colon.

Further, since the maximum resolution is obtained at a distance of about 4.2 mm, the present embodiment enables the distal end of the treatment tool 28 to come into view at a considerably shorter object distance. Projecting the treatment tool 28 further forward allows the distance for the maximum resolution to be reached. Accordingly, at the distance for the maximum resolution, the present embodiment enables the distal end of the treatment tool 28 to sufficiently come into view. This is effective in allowing the treatment tool 28 to be manipulated relatively easily.

Moreover, even at an object distance of 50 mm, the present embodiment enables a subject comprising a 0.5-mm pitch black and white band pair to be viewed on the monitor 5 as is the case with the conventional endoscopes. This enables both a distant view and a close-up view to be observed without the need for complicated operations.

Moreover, when the treatment tool 28 is inserted so that its distal end is displayed on the monitor 5, the illumination light quantity of the light source device 3 is controlled so as to optimize the brightness of vicinity of the treatment tool 28. This facilitates treatment.

Here, in the present embodiment, the CCD 18 has a pixel pitch of 2.5 μm and an effective pixel count of 810 thousand. The image capturing unit 19 has a maximum angle of view of 138° and offers the best resolution at a distance of 4.2 mm. The distance between the optical axis O of the image capturing unit 19 and the center of the distal end opening 26 is 6 mm. However, the present invention is not limited to these values.

Similar effects are also produced in the following case. The pixel pitch, the effective pixel count, the maximum angle of view, and the like are varied so that for example, when an image of a subject comprising a 35-μm pitch black and white band pair is captured, a difference of at least 10% occurs between an output signal obtained from a pixel at which an image of the white subject is captured and an output signal obtained from a pixel at which an image of the black subject is captured. Further, the maximum angle of view and the distance between the optical axis O of the image capturing unit 19 and the center of the distal end opening 26 are varied so that at an object distance at which when an image of the 35-μm pitch subject is captured, the difference between the output signals is at least 10%.

Further, in the above description, the CCD 18 has an effective pixel count of 810 thousand. However, with the mosaic color filter scheme, similar effects are produced at an effective pixel count of about 850 thousand. In this case, the distance for the best resolution can further be increased.

On the other hand, with more then 850 thousand pixels, a practical depth of field cannot be obtained and an attempt to achieve the best resolution results in the insufficient depth of the far point. If the depth of the far point is set at a sufficient value, the best resolution cannot be achieved unless the black and white band pair has a pitch of at least 40 μm.

Further, the present embodiment has been described in conjunction with the color CCD based on the complementary-color mosaic filter scheme. However, the present invention is not limited to this. Similar effects can be exerted by the following scheme, which may be used for electronic endoscopes, provided that the above conditions are met: three-primary-color light of a switching type or the like is used as illumination light, and a monochromatic (black and white) CCD captures an image of a subject in synchronism with sequential emission of the three-primary-color light, with the captured image colorized by the image processing device.

This scheme can provide an R signal, a G signal, and a B signal as CCD output signals for an effective pixel count of about 350 thousand. These signals can be output to the monitor 5 without generating any brightness signal, but in this case, the G signal, having the highest brightness, may be considered to be a brightness signal.

The angle of view is preferably at least 100°, which is determined taking the observability of the peripheries into account and which is used for common endoscopes. A larger angle of view is effective in reducing the distance required to detect the treatment tool.

Further, in the description of the present embodiment, the image processing device 4 and the monitor 5 support video signals based on the HDTV scheme. However, the present invention is not limited to this. A display scheme, for example, SVGA or XGA, may be used which supports a high-resolution monitor.

Moreover, for the image capturing unit 19 according to the present embodiment, heat radiation is disclosed in which heat is radiated to the distal end member of the insertion unit 7 through the heat radiation member 35 and heat radiation cable 36, serving as means for radiating heat from the CCD 18. However, instead of providing the heat radiation cable 36 to the heat radiation member 35, a thermally conductive part of the distal end member of the insertion unit 7 may be placed near and opposite the heat radiation member so that heat can be radiated via a thermally conductive sealing resin or the like.

Alternatively, a part of the signal cable 21 may be used as the heat radiation cable 36. For example, a dummy cable that is not used for driving may be used in the signal cable 21 or an external shield may be used in order to electromagnetically shield the signal cable 21. Alternatively, similar effects are produced by fixing a conductor portion of the heat radiation cable 36 to the vicinity of the CCD chip 18a via a conductive sealing resin without providing the heat radiation member 35.

Further, the chip 18a can be effectively prevented from generating heat by placing an output stage provided inside the CCD chip 18a, on the CCD substrate 18b as an external amplifier, and allotting the power consumption to parts on the external substrate.

Embodiment 2

Now, Embodiment 2 of the present invention will be described with reference to FIGS. 7 to 10. The present embodiment has the same basic configuration as that of Embodiment 1 but differs from Embodiment 1 in the effective pixel count of the CCD, the objective lens system, and the positional relationship between the image capturing unit and the treatment tool channel. The description below focuses on the differences.

The present embodiment is configured as described below.

Figure 7:
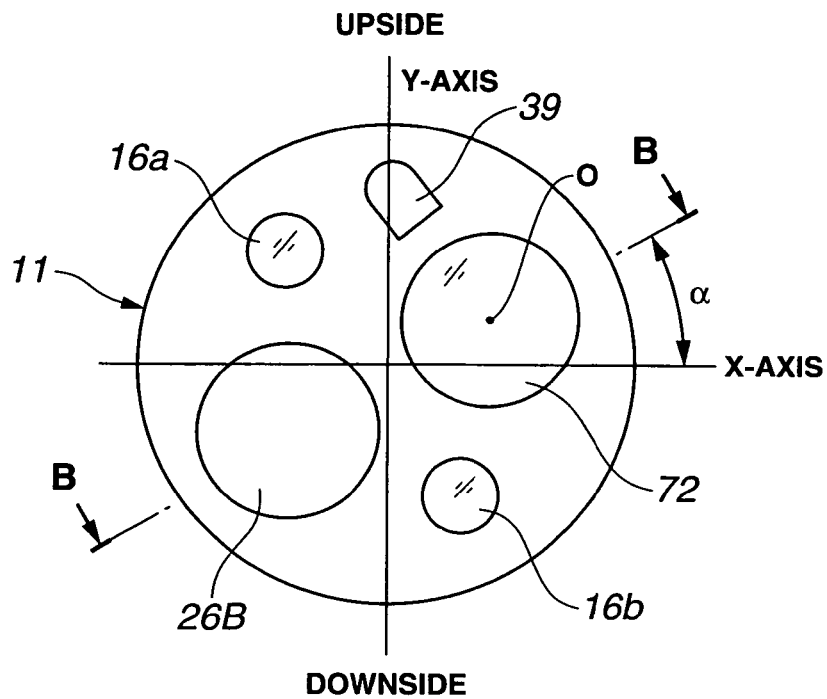
FIG. 7 is a diagram showing the appearance of the distal end surface of a distal end of an insertion unit in Embodiment 2 as viewed from the front.
Figure 8:
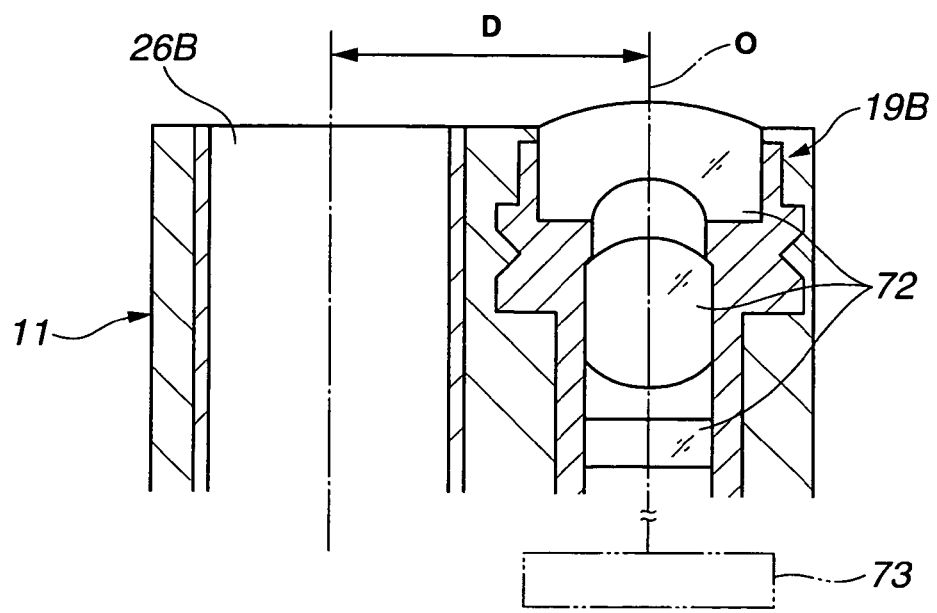
FIG. 8 is a schematic sectional view taken along line B-B in FIG. 7.

An image capturing unit 19B comprising an objective lens 72 and a CCD 73 shown in FIG. 7 or 8 is adopted for the distal end portion 11 of an electronic endoscope according to the present embodiment.

The CCD 73 adopted has a pixel count of 400 thousand which is effective for monitor display at a pixel pitch of 3.3 μm and a maximum image height of about 1.29 mm on the CCD light receiving surface.

Further, in the image capturing unit 19B, a meniscus-shaped lens is placed at the front position of a single-focus objective lens system 72 with a maximum angle of view of 160°. The objective lens system 72 is set to have an Fno of 9.18 so as not to exceed the light diffraction limit. The focus is adjusted so as to obtain the maximum resolution at an object distance of 2.95 mm.

Lens data on the objective lens system 72, used in the present embodiment, is shown below.

| F1 = 1.13723 mm | | | | |
|---|---|---|---|---|
| Surface No. | Ra | Da | Ne | Vd |
| 1 | 8.200 | 0.35 | 1.88815 | 40.8 |
| 2 | 0.910 | 0.66 | | |
| 3 | ∞ | 0.40 | 1.52498 | 59.9 |
| 4 | ∞ | 0.28 | | |
| 5 | 6.994 | 1.91 | 1.77621 | 49.6 |
| 6 | −2.210 | 0.03 | | |
| 7 | ∞ (aperture) | 0.03 | | |
| 8 | ∞ | 0.60 | 1.51965 | 75.0 |
| 9 | ∞ | 1.01 | | |
| 10 | 3.288 | 1.35 | 1.73234 | 54.7 |
| 11 | −1.630 | 0.35 | 1.93429 | 18.9 |
| 12 | −5.110 | 0.53 | | |
| 13 | ∞ | 0.03 | | |
| 14 | ∞ | 1.00 | 1.51825 | 64.1 |
| 15 | ∞ | 0.01 | 1.51193 | 63.0 |
| 16 | ∞ | 1.00 | 1.61379 | 50.2 |
| 17 | ∞ | 0.00 | | |

As shown in FIG. 7, the following are disposed in the distal end portion 11 of the insertion unit: the image capturing unit 19B including an objective lens system 72 which has a meniscus-shaped distal end lens with an outer diameter of φ2.8 mm, a channel distal end opening 26B, the air and water supply nozzle 39 that supplies air and water to the distal end surface of the objective lens system 72 to remove contaminants adhering to the surface, and the illumination lenses 16a and 16b used to illuminate a subject with light having passed through the light guide (not shown) connected to the light source device 4.

The image capturing unit 19B is attached to the distal end of the insertion unit so that the up-down direction on the monitor 5 observed when a captured image of the subject is displayed on the monitor matches the up-down direction at the distal end of the insertion unit shown in FIG. 7.

The treatment tool channel 25 with an inner diameter of φ2.8 mm is placed below and obliquely leftward of the image capturing unit 19B; this direction slightly deviates from a horizontal direction. As shown in FIG. 7 when the up-down direction of the distal end portion 11 is assumed to align with the Y axis, while the right-left direction of the distal end portion 11 is assumed to align with the X axis, the straight line joining the center axis of the treatment channel 25 with the optical axis O of the image capturing unit 19B forms an angle α to the X axis.

As shown in FIG. 8, the optical axis O of the objective lens system 27 is placed parallel to the distal end opening 26B. In the present embodiment, the distance D between the center (optical axis) of the objective lens system 72 and the center axis of the distal end opening 26B is 6 mm.

Next, effects of the present embodiment will be described.

First, description will be given of effects of the present embodiment exerted when the image capturing unit 19B is used to capture an image of a subject comprising a 35-µm pitch black and white band pair.

When the image capturing unit 19B configured as described is used to capture an image of the subject comprising the 35-µm pitch black and white band pair at an object distance of 2.95 mm, at which the best resolution is obtained, the black and white bands formed on the CCD light receiving surface have a contrast G of 11.5%.

A photoelectric conversion is executed on the image of the subject comprising the 35-µm pitch black and white band pair which image has been formed on the light receiving surface of a CCD 73 via the objective lens system 72. A difference of approximately 11.5% occurs between an image signal output by a pixel at which an image of the white band is formed and an image signal output by a pixel at which an image of the black band is formed.

The image signals are input to the image processing unit 47 via the CDS circuit 44, A/D converter 45, and signal processing unit 46. For example, a gamma process suitable for the monitor, an electric mask process, or the like is then executed so that the black and white belts have a contrast I of at least 10%.

This enables the image of the 35-µm pitch black and white band pair captured by the image capturing unit 19B to be viewed on the monitor as a black and white band pair.

Further, if the image capturing unit 19B according to the present embodiment is used to capture an image of a subject comprising a 0.5-mm pitch black and white band pair and placed at an object distance of 50 mm, the black and white bands formed on the light receiving surface of the CCD 73 have a contrast G of 19.3%.

A photoelectric conversion is similarly executed on the image of the subject comprising the 0.5-mm pitch black and white band pair which image has been formed on the light receiving surface of a CCD 73. A difference of approximately 19.3% occurs between an image signal output by a pixel at which an image of the white band is formed and an image signal output by a pixel at which an image of the black band is formed. The signals are processed by the image processing unit 4 so that the black and white bands have a contrast I of at least 10%. The resulting signals are output to the monitor 5.

This enables the image of the 0.5-mm pitch black and white band pair placed at a distance of 50 mm and captured by the image capturing unit 19B to be viewed on the monitor 5 as black and white bands.

Figure 9:
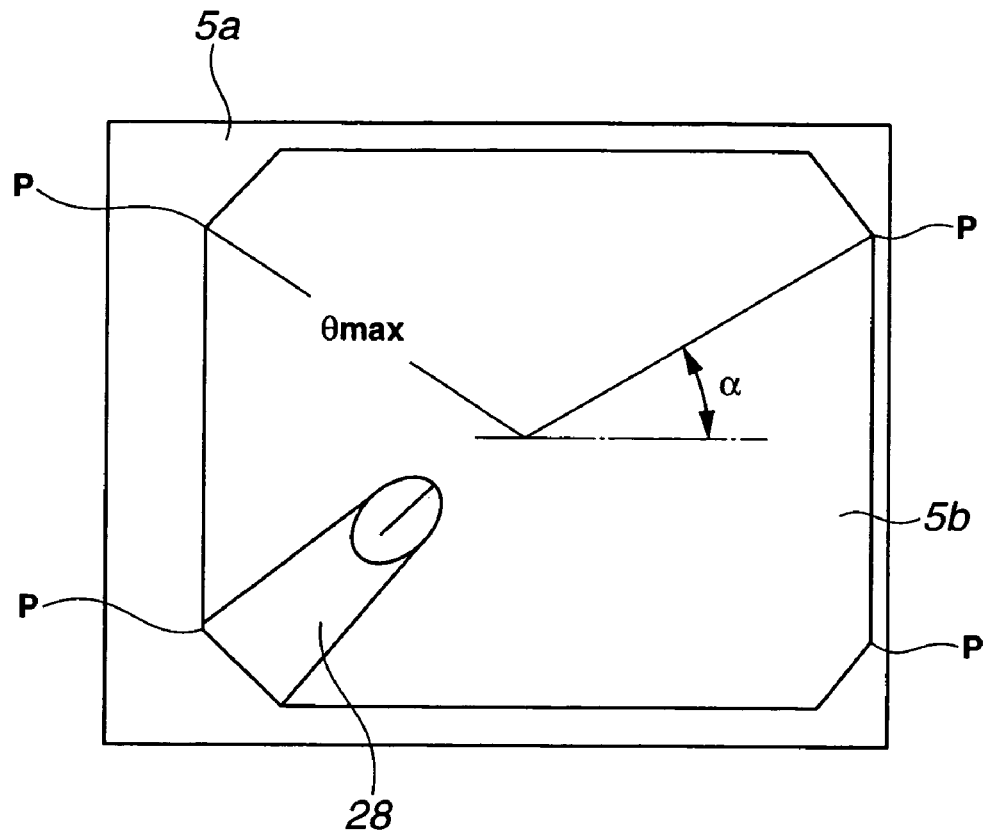
FIG. 9 is a diagram showing a monitor display picture obtained when a treatment tool inserted through a channel in Embodiment 2 is projected from a distal end.
Figure 10:
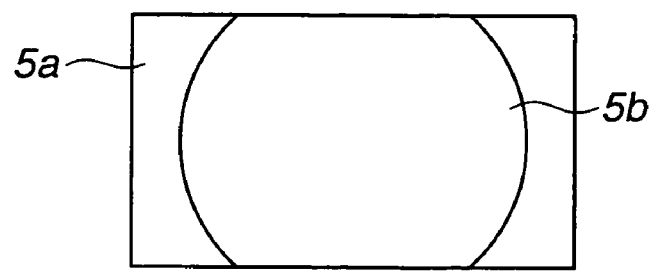
FIG. 10 is a diagram showing a display area of an endoscope according to a variation.

The above electric mask process involves creating an octagonal display area 5b with an aspect ratio of 1:1.2 as shown in FIG. 9 and displaying an image of the subject captured by the image capturing unit 19B, in the octagonal display area 5b.

For such a laterally elongate display area as shown in FIG. 9, the angle of view on the display area 5b resulting from the above electric mask process is largest when formed of diagonal points P (θmax). The mask process is executed so that the angle of view of 160° of the objective lens system 72 is equal to the maximum angle of view θmax. On the other hand, the mask process is executed so that the smallest angle of view on the monitor screen is in the up-down direction and the second smallest angle of view is in the right-left direction.

The points P, constituting the maximum diagonal angle, is set so that an angle α is formed between the straight line joining the point P and the screen center and the horizontal direction on the monitor screen. Moreover, the image capturing unit 19B is set so that the X axis direction on the distal end portion 11 of the insertion unit aligns with the horizontal direction of the monitor as shown in FIG. 7. Consequently, the treatment tool 28 projected from the distal end opening 26B of the treatment tool channel 25 placed at the angle α to the X axis is displayed in a part of the display area 5b which is located, roughly speaking, below the horizontal direction on the monitor 5, and more strictly speaking, slightly below the horizontal direction, so that the treatment tool 28 extends from the lower left point P, as shown in FIG. 9.

Description will be given of conditions for allowing the image capturing unit 19B to capture an image of the treatment tool 28 projected from the distal end opening 26B in the distal end portion 11 of the insertion unit according to the present embodiment. If the treatment tool 28 projects from the distal end surface of distal end portion 11 by the minimum amount, that is, if the treatment tool 28 is shifted closest to the image capturing unit 19B, the minimum projection amount Hmin is derived from the light height Lh=1.31 mm on the distal end lens surface of the image capturing unit 19B, the radius R=2.8 mm of the distal end opening 26B, the angle of view θ=160° of the image capturing unit 19B, and the distance D=6 mm between the optical axis O of the image capturing unit 19B and the channel 25 as shown in Equation 3.

$$H\min=(D-Lh-R)\times\tan(90°-\theta/2)=0.58 \text{ mm} \quad \text{(Equation 3)}$$

On the other hand, if the treatment tool 28 is positioned at the largest distance from the image capturing unit 19B, the condition for allowing the image capturing unit 19B to capture an image of the entire distal end of the treatment tool 28, that is, the amount Hall of projection of the treatment tool 28 from the distal end surface of distal end portion 11, is derived as shown in Equation 4.

$$H\text{all}=(D-Lh+R)\times\tan(90°-\theta/2)=1.07 \text{ mm} \quad \text{(Equation 4)}$$

As shown in Equations 3 and 4, the treatment tool 28 starts to come into the view of the image capturing unit 19B when the amount of projection of the distal end portion 11 from the distal end surface is at least 0.58 mm. When the distal end portion 11 is projected by 1.07 mm, almost the entire distal end of the treatment tool 28 comes into the view of the image capturing unit 19B.

Thus, at an object distance of 2.95 mm, at which the image capturing unit 19B according to the present embodiment offers the best resolution, the distal end of the treatment tool 28 is ensured to come into the view of the image capturing unit 19B. Consequently, the distal end can also be viewed on the monitor 5.

The present embodiment exerts the effects described below.

The present embodiment adopts the single-focus optical system as an objective optical system constituting the image capturing unit 19B. This enables the structure of the image capturing unit 19B to be simplified compared to that of a resizing optical system or a variable-focus optical system.

The present embodiment offers the best resolution at a shorter distance of 2.95 mm. This serves to increase the display scale on the monitor, allowing the subject to be more easily observed.

In the present embodiment, the CCD 73 has a pixel pitch of 3.3 μm and an effective pixel count of 400 thousand. The image capturing unit 19B has a maximum angle of view of 160° and offers the best resolution at a distance of 2.95 mm. The distance between the optical axis O of the image capturing unit 19B and the center of the distal end opening 26 is 6 mm. However, the present invention is not limited to these values.

Similar effects are also produced in the following case. The pixel pitch, the effective pixel count, the maximum angle of view, and the like are varied so that for example, when an image of a subject comprising a 35-μm pitch black and white band pair is captured, a difference of at least 10% occurs between an output signal obtained from a pixel at which an image of the white subject is captured and an output signal obtained from a pixel at which an image of the black subject is captured. Further, the maximum angle of view and the distance between the optical axis O of the image capturing unit 19 and the center of the distal end opening 26 are varied so that at an object distance at which when an image of the 35-μm pitch subject is captured, the difference between the output signals is at least 10%.

Further, in the present embodiment, the effective pixel count is 400 thousand. However, with the mosaic color filter scheme, similar effects are produced with about 250 thousand pixels. This is also effective in enabling an increase in the distance for the best resolution and in the display scale on the monitor 5. On the other hand, with less than 250 thousand pixels, the distance for the best resolution is about 2 mm. This may degrade treatability.

The present embodiment can also adopt the scheme of using three-primary-color light of a switching type or the like as illumination light and using a monochromatic (black and white) CCD to capture an image of a subject in synchronism with sequential emission of the three-primary-color light, with the captured image colorized by the image processing device. In this case, effects similar to those of the mosaic filter scheme with 250 thousand pixels are exerted using a CCD with an effective pixel count of about 100 thousand.

In the present embodiment, as shown in FIG. 9, the display area 5b of the monitor screen 5a is shaped like a laterally elongate octagon having a display size that is longer in the horizontal direction than in the vertical direction. However, the present invention is also applicable to the case where the mask process is executed so as to increase the horizontal size, that is, so as to form a circle and not executed in the vertical direction as in the case of the display area 5b in a variation shown in FIG. 10. That is, also in this case, the projecting distal end of the treatment tool may appear from a substantially horizontal direction in which the display area size (display area) is larger and may extend through the display area 5b.

Further, more generally, the distal end opening may be located in association with the direction in the display area in which the display area is larger so that the treatment tool 28 projecting from the distal end opening can be displayed in the direction in which the display area is larger.

The direction in which the display area is larger is the direction on which reduced limitation is imposed (visual field is larger) if the direction in which observed images are viewed is limited. For example, if the visual field for observed images is limited in association with a substantially vertical direction on the monitor, the distal end opening of the channel may be located in association with a direction similar to the substantially horizontal direction.

Further, in the above description, the image processing device 4 and the monitor 5 in the present embodiment support video signals based on the HDTV scheme. However, the present invention is not limited to this. The image processing device 4 and the monitor 5 may support video signals based on, for example, the NTSC scheme or the PAL scheme. Furthermore, video signals based on the VGA scheme or the SVGA scheme may be used.

The above embodiments adopt the single-focus objective optical system. However, description will be given below of, for example, an endoscope that adopts a focal-point-variable objective optical system.

Embodiment 3

Next, with reference to FIGS. 11 to 18, a third embodiment of the present invention will be explained.

Figure 11:
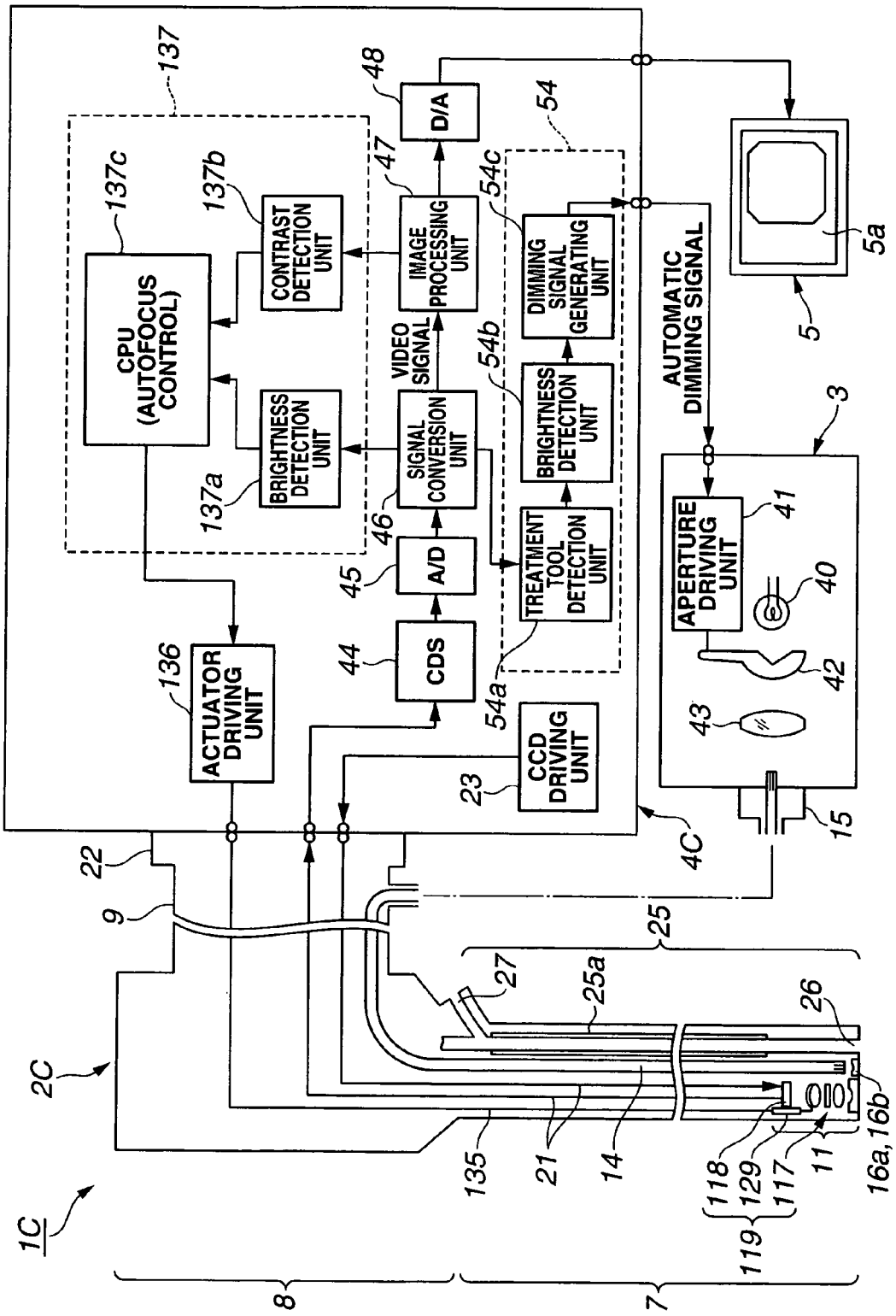
FIG. 11 is a diagram showing the general configuration of an electronic endoscope system comprising Embodiment 3 of the present invention.

As shown in FIG. 11, an electronic endoscope system 1C comprises an electronic endoscope 2C of the third embodiment, light equipment 3 which supplies illumination light to this electronic endoscope 2C, an image processing apparatus (signal processing apparatus) 4C which performs signal processing to image pickup means embedded in the electronic endoscope 2C, and a monitor 5 corresponding to a Hi-Vision TV (this is abbreviated as HDTV) system, showing an endoscope image, by inputting a standard video signal outputted from the image processing apparatus 4C.

The electronic endoscope 2C of this embodiment has an insertion unit 7 which is slender and is inserted into a test object, an operation unit 8 which is provided in a rear end of this insertion unit 7, and which an operator such as an expert holds and operates, and a cable portion 9 extended from this operation unit 8.

A rigid distal end portion 11 is provided in an end of the insertion unit 7, and an image pickup unit 119 and the like which are mentioned later are provided in this distal end portion 11.

In the insertion unit 7, a light guide 14 which transmits illumination light is inserted, and a rear end side of this light guide 14 extends through the cable portion 9 to a light guide connector 15 provided in its end portion. When an operator connects this light guide connector 15 to the light equipment 3, illumination light is supplied to a rear end surface of the light guide 14 from the light equipment 3.

The illumination light supplied from the light equipment 3 is transmitted by the light guide 14, and is further emitted forward through illumination lenses 16a and 16b (refer to FIG. 14) mounted on an illumination window with facing the end surface fixed to the distal end portion 11 to illuminate objects such as an affected part in a body cavity. An observation window (or image pickup window) is provided in the distal end portion 11 adjacent to the illumination window, and on this image pickup window is provided, an image pickup unit 119 comprising an objective lens system (or an objective optical system) 117 which images an optical image of an illuminated object, and, for example, a charge coupled device (this is abbreviated as a CCD) 118 as an image pickup device whose light-receiving surface (or photo-electric conversion surface) is arranged at an image forming position of this objective lens system 117.

One end of a signal cable 21 is connected to the image pickup unit 119, the signal cable 21 inserted into the insertion unit 7 is further inserted inside the cable portion 9, and another end is connected to a signal connector 22 in its rear end.

By connecting this signal connector 22 to the image processing apparatus 4C, the CCD 118 is driven with a CCD drive signal from a CCD driving unit 23 of the image processing apparatus 4C, and the CCD 118 outputs an image signal (image pickup signal) which performed photo-electric conversion.

A video signal is generated by this image pickup signal being given signal processing in the image processing apparatus 4C, and an endoscope image is shown on the monitor 5.

In addition, in the insertion unit 7, a channel 25 which makes various treatment tools insertable is provided. This channel 25 comprises a channel distal end opening (this is also called a distal end opening or a forceps opening) 26 which opens in the distal end portion 11, a treatment tool insert port 27 near a front end of the operation unit 8, and a channel tube 25a which connects the distal end opening 26 and the treatment tool insert port 27.

Then, by inserting a treatment tool 28 from this treatment tool insert port 27, it is made possible to protrude an end side of this treatment tool 28 from the distal end opening 26, and to pick up affected part tissue or to deal with resection and the like, with the end side of the treatment tool 28.

Furthermore, in this embodiment, it is made possible to perform treatment and the like smoothly by showing not only an object to be a test objects or a treatment object such as affected part tissue, but also the projecting treatment tool 28 on a screen of the monitor 5 with putting the end side of the treatment tool 28, protruded from the distal end opening 26, in a visual field of the image pickup unit 119.

In this embodiment, the CCD 118 is a mosaic color filter type CCD equipped with a complementary mosaic color filter, and a pixel pitch is 2.5 µm and a pixel count effective in monitor display is 1,300,000 pixels.

Figure 12:
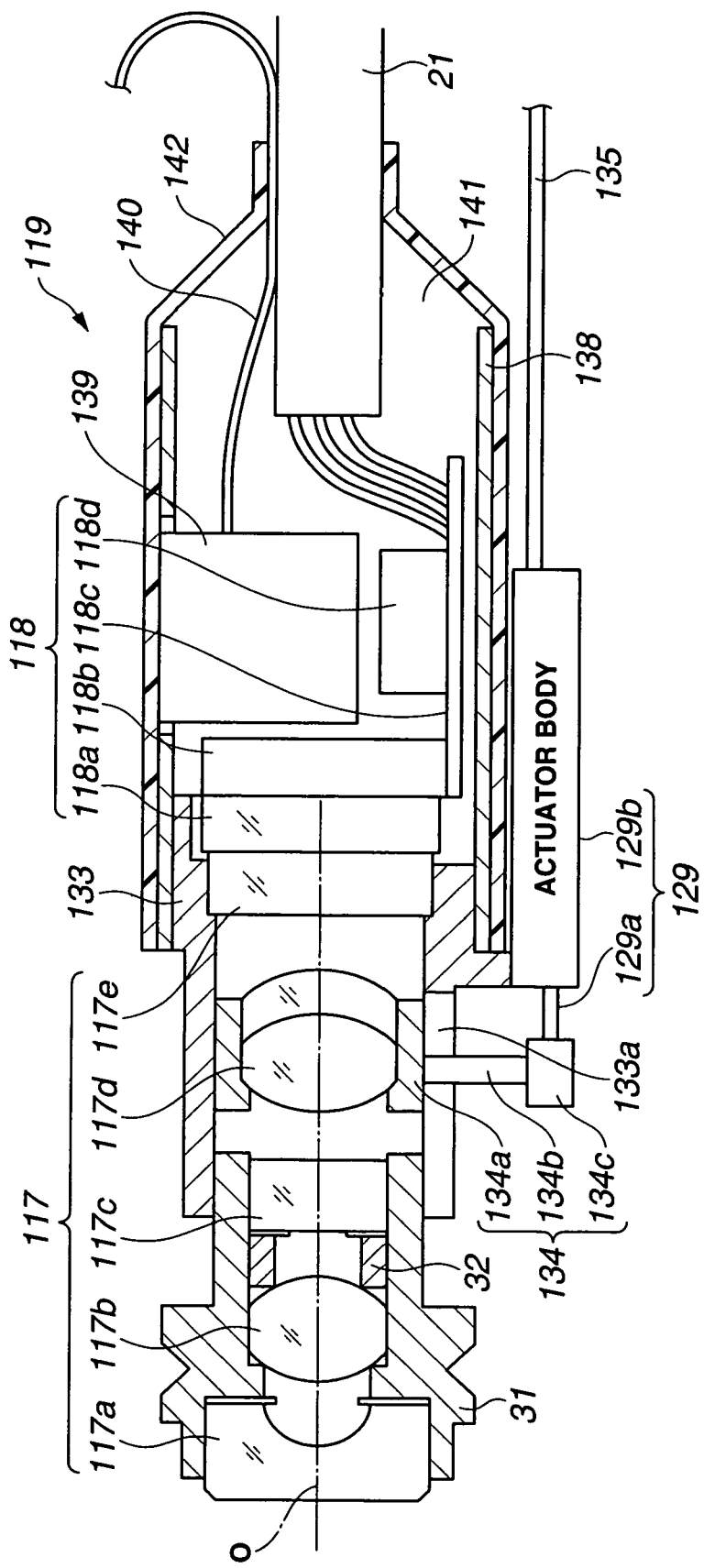
FIG. 12 is a sectional view of an image capturing unit in the electronic endoscope according to Embodiment 3.
Figure 13:
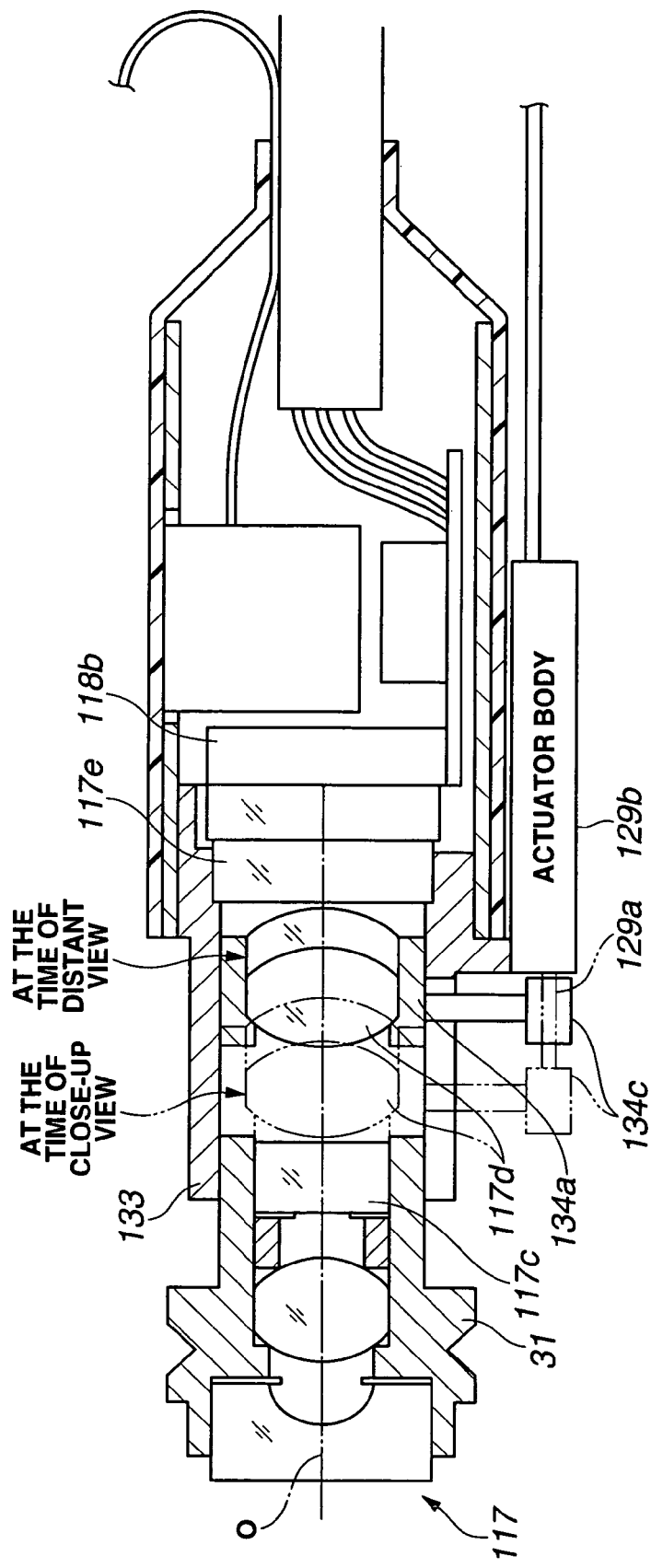
FIG. 13 is a diagram showing the appearance of the distal end surface of a distal end of an insertion unit in Embodiment 3 as viewed from the front.

In the above-mentioned image pickup unit 119, since the objective lens system 117 which is constructed of a varifocal optical system where an angle of view hardly changes when changing a focal position whose maximum angle of view is about 120° to 140° is used, it is made possible to form an image on the CCD 118 in a high resolution from a close-up view (near point side) to a distant view (far point side) as shown in FIG. 13 by moving forward and backward a doublet 117d on an optical axis O of the objective lens system 117 with an actuator 129 as explained in FIG. 12.

In this objective lens system 117, Fno (F-number) is set at about 10.0 or less so as not to exceed a diffraction limit of light. In addition, it is set so as to obtain the highest resolution when an object distance is at the time of the close-up view.

A configuration of the image pickup unit 119 in this embodiment will be explained using FIG. 12.

A plurality of lenses (including optical elements) 117a, 117b, and 117c which are a prior phase if the objective lens system 117 are fixed to a lens frame 31 after having performed proper spacing and centering of respective lenses.

In the case of FIG. 12, spacing between the lenses 117b and 117c is set by a spacer 32. In addition, the first, second, and third lenses 117a, 117b, and 117c which construct the objective lens system 117 and are arranged sequentially from its end side are a plano-concave lens, a biconvex lens, and an infrared cut-off filter, respectively.

In addition, in a CCD frame 133 fit to this lens frame 31, a lens holding frame portion 134a by which the doublet 117d is held is provided slidably in a direction of the optical axis O of the objective lens system 117.

Furthermore, in this CCD frame 133, a parallel plate lens 117e and a CCD chip 118b are fixed at a position in a rear side of the lens holding frame portion 134a.

The CCD 118 comprises a sealing glass 118a, the CCD chip 118b whose light-receiving surface (image pickup plane) is protected by this sealing glass 118a, a CCD substrate 118c connected to the CCD chip 118b, and CCD drive parts 118d implemented in this CCD substrate 118c.

The CCD substrate 118c is electrically connected to the CCD chip 118b with bump connection or the like. In addition, on the CCD substrate 118c, the CCD drive parts 118d, such as a coupling capacitor and a transistor for current amplification, are soldered. The sealing glass 118a for protecting the light-receiving surface of the CCD chip 118b is fixedly bonded on this light-receiving surface with an optical adhesive or the like.

The lens frame 31 is fit with the CCD frame 133 so as to be movable in parallel 1 in the direction of the optical axis of the objective lens system 117, and the CCD chip 118b is fixedly bonded to the CCD frame 133 so that the optical axis of the above-described objective lens system 117 and the light-receiving surface of the above-described CCD chip 118b may become perpendicular.

In addition, in this example, the doublet 117d with, for example, positive power (refractive power) which is arranged in the CCD frame 133 is held by the lens holding frame portion 134a which fits to an inner peripheral surface of the CCD frame 133 and becomes movable, and this lens holding frame portion 134a is connected to an actuator connecting portion 134c outside the CCD frame 133 through an arm portion 134b which penetrates the inside of a long groove 133a provided in the CCD frame 133.

A moving lens frame 134 which moves the doublet 117d is formed of the above-mentioned lens holding frame portion 134a, arm portion 134b, and actuator connecting portion 134c.

Furthermore, an actuator 129 which moves the doublet 117d with the moving lens frame 134 through the actuator connecting portion 134c comprises an actuator moving portion 129a connected to the actuator connecting portion 134c, and an actuator body 129b which moves this actuator moving portion 129a in a direction parallel to the optical axis O of the objective lens system 117. This actuator body 129b is fixed by an outer periphery side of the CCD frame 133.

This actuator body 129b is connected to an actuator driving unit 136 (refer to FIG. 11) provided in the image processing apparatus 4C through a signal line 135, and the actuator body 129b operates with an actuator drive signal from this actuator driving unit 136. It is made that the actuator body 129b can move the actuator moving portion 129a to a rear side, which becomes in a side of the actuator body 129b, according to this actuator drive signal, and can move it to a front side separated from the actuator body 129b. This actuator driving unit 136 generates (outputs) an actuator drive signal corresponding to a control signal from the CPU 137C which constructs an auto-focusing unit (a focus control unit in this embodiment) 137 provided in the image processing apparatus 4C.

In a state shown in FIG. 12, the doublet 117d is in a state of being set in an approximately center of a movable range (moving range), and is set at a position shown by an alternate long and two short dashes line in FIG. 13 in the case of a set state at the time of the close-up view that it is moved to a most front side with the actuator drive signal to become in a state of forming an image of the close-up view, which is focused in the near point side, on the CCD chip 118b in a high resolution within a range of 5.2 mm to 10 mm of depth of field in this state.

In addition, when it is moved in the most rear side with the actuator drive signal, the doublet 117d is set at a position in a most rear side shown by a continuous line in FIG. 13, and this state becomes a set state at the time of the distant view which becomes the far point side. In this set state at the time of the distant view, it becomes in a state of focusing on the distant view and forming an image of the distant view on the CCD chip 18b in a predetermined resolution in a state that a depth of field is large, that is, 10 mm to 100 mm.

In this way, the doublet 117d is made possible to perform a moving setup at an arbitrary position within a movable range with making positions from the close-up view to the distant view as the movable range. In addition, since FIG. 13 is a diagram for explanation of operation, and is shown with assigning reference numerals only to a part of components.

As shown in FIG. 12, lands (not shown) for soldering signal lines of the signal cable 21 on the CCD substrate 118c are provided, and the signal lines of the signal cable 21 are soldered. A CCD protective frame 138 protecting mechanically is arranged from the CCD frame 133 to a connecting portion of the signal cable 21 with the CCD substrate 118c through the CCD chip 118b.

In this CCD protective frame 138, a notched portion is provided at a position near a blackface portion of the CCD chip 118b, and a heat radiation member 139 which is good in thermal conductivity and is formed with, for example, an aluminum alloy or a copper alloy is arranged so as to be inserted from this notched portion. A cable 140 for heat radiation where metal being good in thermally conductivity is used as a conductor is mechanically connected to this heat radiation member 139 with soldering, an adhesive, or the like.

Inside the CCD protective frame 138, a sealing resin 141 is filled, and a vicinity of the CCD chip 118b is sealed by a tube 142 with heat shrinkage nature. The cable 140 for heat radiation is soldered to a member with large heat capacity, for example, the distal end portion 11 of the insertion unit 7.

The signal cable 21 is covered with a Teflon (registered trademark) sheath on it after making a plurality of coaxial lines and a plurality of solid wires twisted, wrapping a tape made of a fluorocarbon resin over it, winding copper wire as a package shield over it, and further wrapping a tape made of a fluorocarbon resin over it.

Figure 14:
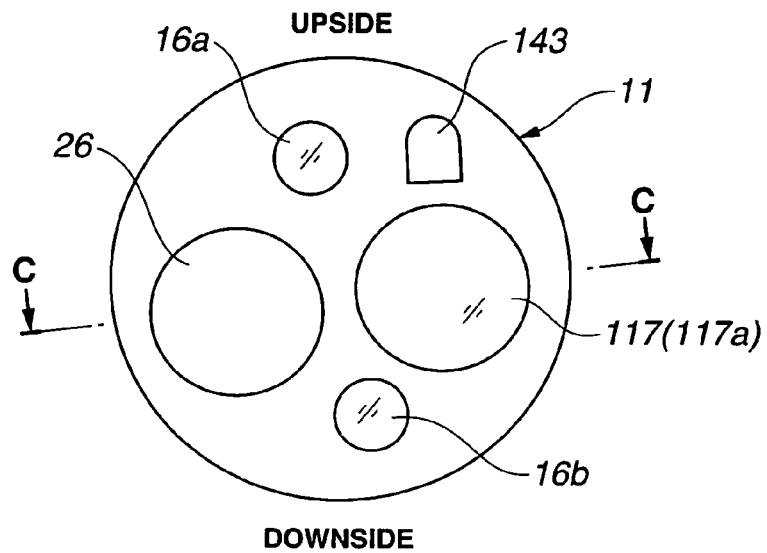
FIG. 14 is a diagram showing the appearance of the distal end surface of the insertion unit distal end of the electronic endoscope according to Embodiment 3 as viewed from the front.

In the distal end portion 11 of the insertion unit 7, as shown in FIG. 14, the image pickup unit 119 which includes the objective lens system 117 that an outer diameter of the first lens 117a in an end is $\phi$2.8 mm, the channel distal end opening 26, an air-supplying and water-supplying nozzle 143 which supplies water and air to an outer surface of the objective lens system 117 to remove a waste material which adheres to it, and the illumination lenses 16a and 16b for illuminating an object with light transmitted (guided) by the light guide 14 connected to the light equipment 3 are provided.

The image pickup unit 119 is mounted on the distal end portion 11 so that a vertical direction on the monitor 5 when an image of an object is picked up and is shown on the monitor 5 may coincide with a vertical direction of the distal end portion 11 of the insertion unit 7 shown in FIG. 14. In addition, for example, a tube with an inner diameter of 2.8 mm which is made of Teflon (registered trademark) is used for the channel tube 25a in this embodiment.

Figure 15:
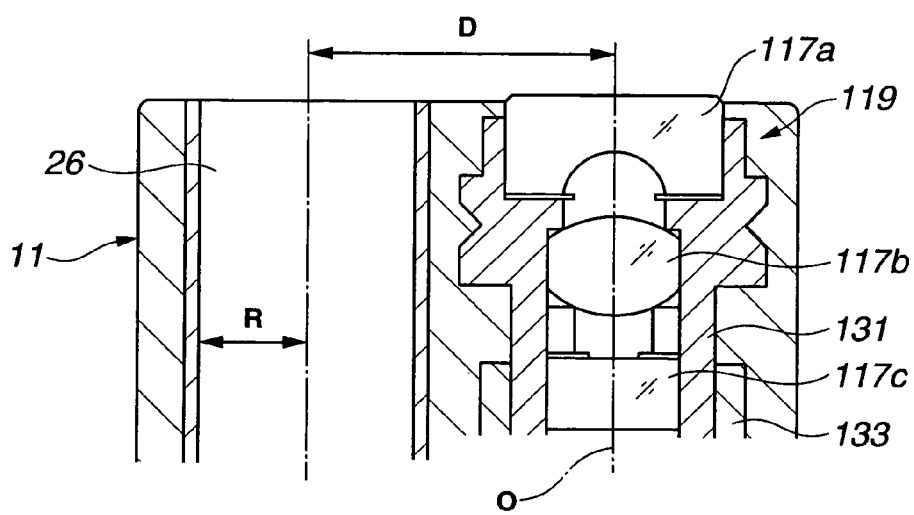
FIG. 15 is a schematic sectional view taken along line C-C in FIG. 14.

As shown in FIG. 15, the optical axis O of the objective lens system 117 and the distal end opening 26 (to which an end of the channel tube 25a is connected) are arranged in parallel, and in this embodiment, a distance D between a center (optical axis O) of the objective lens system 117 and a central axis of the distal end opening 26 is set, for example, to 6 mm. Doubleness of a radius R of this distal end opening 26 is 2.8 mm which is the same as an inner diameter of the channel tube 25a.

As shown in FIG. 11, the light equipment 3 has a lamp 40, and illumination light of this lamp 40 is incident into an incident end face of the light guide 14 in the light guide connector 15 through a condenser lens 43, after transmitted light volume is adjusted by an opening of an aperture 42 driven by an aperture driving unit 41.

Then, the illumination light is further emitted to an object side through the illumination lenses 16a and 16b from an end of the light guide 14 as mentioned above.

In addition, the light guide 14 is branched into two lines in the insertion unit 7, and as shown in FIG. 14, in the distal end portion 11, the illumination light is emitted respectively from the illumination lenses 16a and 16b arranged in two places.

As shown in FIG. 11, the image processing apparatus 4C has a CDS circuit 44 where an image signal from the CCD 118 is inputted, and it is converted into a digital signal by an A/D converter 45 after a signal component is extracted by this CDS circuit 44.

The digital image signal converted by this A/D converter 45 is inputted into a signal conversion unit 46 which generates a video signal which is constructed of a brightness signal and a chrominance signal. The video signal generated by this signal conversion unit 46 is inputted into an image processing unit 47 which performs various image processings such as γ correction. After an output signal of this image processing unit 47 is inputted into a D/A converter 48 and is converted into a video signal corresponding to an analog HDTV system, it is outputted to the monitor 5.

In addition, the brightness signal from the signal conversion unit 46 is inputted into an automatic dimming unit 54 which generates an automatic dimming signal, and the automatic dimming signal is generated by this automatic dimming unit 54. This automatic dimming unit 54 comprises a treatment tool detection unit 54a which detects a treatment tool, a brightness detection unit 54b which detects an average level of the brightness signal inputted from this treatment tool detection unit 54a, and a dimming signal generating unit 54c which compares the average level of the detected brightness signal with a reference value which becomes a reference and outputs a difference signal from the reference value as an automatic dimming signal.

The treatment tool detection unit 54a detects, for example, with reflected light volume and color of a treatment tool that the treatment tool enters in a visual field of the image pickup unit 119 (in other words, an image of the treatment tool is formed on the light-receiving surface of the CCD 118).

Furthermore, the brightness detection unit 54b detects peak brightness (light volume) near in a region where an image of a treatment tool is formed, and mean brightness (light amount) near this region when the treatment tool is detected in the treatment tool detection unit 54a.

Moreover, this brightness detection unit 54b detects peak brightness and mean brightness in a whole screen when a treatment tool is not detected in the treatment tool detection unit 54a.

In addition, the dimming signal generating unit 54c generates an automatic dimming signal which adjusts illumination light volume of the light equipment 3 so that an signal with proper brightness may be obtained by the peak brightness or mean brightness signal from the brightness detection unit 54b, and outputs it to the aperture driving unit 41 of the light equipment 3.

The automatic dimming signal of the automatic dimming unit 54 is inputted into the aperture driving unit 41 of the light equipment 3, and the aperture driving unit 41 adjusts an opening amount of the aperture 42 automatically according to the automatic dimming signal and performs control so as to obtain an image with brightness which is suitable for observation and is equivalent to the reference value of the dimming signal generating unit 54c.

Furthermore, the brightness signal of the signal conversion unit 46 is inputted into a brightness detection unit 137a which constructs the auto-focusing unit 137, and brightness of an image is detected by the brightness detection unit 137a.

Moreover, an output signal of the image processing unit 47 is inputted into a contrast detection unit 137b which constructs the auto-focusing unit 137, and contrast of the output signal is detected by the contrast detection unit 137b.

Brightness information detected by the brightness detection unit 137a and contrast information detected by the contrast detection unit 137b are inputted into the CPU 137C, this CPU 137C performs, for example, hill-climbing type auto-focus control (this will be mentions later in FIG. 16) by brightness information and contrast information.

The electronic endoscope 2C of this embodiment adopts a varifocal optical system (thus, a variable focal position optical system) where focal length changes without an angle of view hardly changing according to movement by arranging a part of the doublet 117d in the objective lens system 117 movably in a direction of the optical axis O, and making it continuously movable within a range from a position at the time of a close-up view to a position at the time of a distant view.

Then, by performing focus control of this doublet 117d by the auto-focusing unit 137 to set it in an always-focused state within a range from the close-up view to the distant view, it is made possible to pick up an image in a state of keeping a high resolution and a predetermined depth of field.

In addition, as explained below, this embodiment adopts the configuration that it is easy to secure a large angle of visibility (angle of view) even when it is set as the close-up view, and to perform fine treatment with keeping an end side of a treatment tool, protruded from the distal end opening 26 of the channel 25, within a visual field also when the treatment tool is used.

Specifically, in this embodiment, when the end side of the treatment tool 28 inserted in the channel 25 is protruded from the distal end opening 26, it is made that the end side of the treatment tool 28 enters in a visual field of the image pickup unit 119 in an object distance in a side of a close-up view that a high resolution of making, for example, black and white in a 35-μm pitch discriminable is obtained, and in other words, that an image of the end side of the treatment tool 28 is formed on the light-receiving surface of the CCD 118.

An operation of this embodiment by such configuration will be explained below.

As shown in FIG. 11, the light guide connector 15 of the electronic endoscope 2C is connected to the light equipment 3, and the signal connector 22 is connected to the image processing apparatus 4C. In addition, a cable of the monitor 5 is connected to a video output terminal of this image processing apparatus 4C to make it possible to perform endoscopy.

Then, a power switch which is not shown is turned ON for illumination light from the light equipment 3 to be supplied to the light guide 14, and the illumination light is emitted from the illumination lenses 16a and 16b through the light guide 14 to make it possible to illuminate an object an image of which is picked up with the image pickup unit 119. In addition, it is made in a state that an image image-captured with the CCD 118 of the image pickup unit 119 is shown on the monitor 5 through the image processing apparatus 4C.

Next, the insertion unit 7 of the electronic endoscope 2C is inserted into a patient's body cavity, and the distal end portion 11 of the insertion unit 7 is made in a state that an object of a region, which is given endoscopy, such as an affected part in the body cavity can be observed. In this case, the objective lens system 117 in the image pickup unit 119 provided in the distal end portion 11 forms an optical image of the object on the light-receiving surface of the CCD 118. The image which is imaged on the light-receiving surface of the CCD 118 is given photo-electric conversion to be converted into an image signal.

The image signal is inputted into the CDS circuit 44 of the image processing apparatus 4C through the signal cable 21 and the signal connector 22. This image signal has a waveform including reset noise and the like besides signal components, and a signal in a baseband where the signal components are extracted is generated by the CDS circuit 44.

An output signal of this CDS circuit 44 is inputted into the A/D converter 45, and the A/D converter 45 converts into a digital signal the image signal which is an analog signal. The image signal converted into the digital signal is converted into a video signal by the signal conversion unit 46.

In this case, since a complementary mosaic color filter is adopted as the CCD118 in this embodiment, this signal conversion unit 46 converts into, for example, video signals such as a brightness signal which is obtained by averaging signal outputs of pixels of adjacent four kinds of color filters, and color-difference signals obtained from differences between pixel signal outputs of respective colors.

The video signals are given contrast adjustment, color adjustment, display size adjustment, and the like which are suitable for monitor display by the image processing unit 47.

Then, the D/A converter 48 converts it into a video signal corresponding to an analog HDTV system which can be shown on the monitor 5. The monitor 5 shows an image of an object (image-captured by the CCD 118), corresponding to the inputted HDTV video signal, on a monitor screen 5*a*.

First, an automatic dimming function will be explained.

When the treatment tool 28 is not included in a visual field of the image pickup unit 119, the automatic dimming unit 54 detects brightness (specifically, peak brightness or mean brightness) of a whole screen by the brightness detection unit 54*b*, and outputs it to the dimming signal generating unit 54*c*. This dimming signal generating unit 54*c* outputs a control signal, and specifically, an automatic dimming signal to the light equipment 3 so as to increase brightness when a screen is dark. In addition, when the screen is too bright, it outputs the automatic dimming signal as a control signal which controls the light equipment 3 so as to perform dimming.

With the automatic dimming signal, the aperture driving unit 41 in the light equipment 3 drives the aperture 42 to adjust volume of illumination light which is incident into a rear end of the light guide 14 through the aperture 42 from the lamp 40 so as to become proper light volume.

Next, an operation of the automatic dimming in the case that the treatment tool 28 is used for tissue extraction for therapy or for resection of a lesioned part in the endoscopy for an object such as an affected part by the image pickup unit 119 will be explained.

By inserting the treatment tool 28 into the channel 25 to protrude the treatment tool 28 through the distal end opening 26 of the distal end portion 11 of the insertion unit 7 from its end surface, the treatment tool enters in the visual field of the image pickup unit 119.

In this case, the treatment tool detection unit 54*a* detects, for example, from color of the treatment tool 28, reflected light of the treatment tool 28, or the like that the treatment tool 28 enters in the visual field, and detects brightness in peak brightness or mean brightness in a certain region about the above-described treatment tool 28 as a center. The dimming signal generating unit 54*c* outputs the automatic dimming signal as a control signal so as to dim the light of the light equipment 3 when the brightness around the above-described treatment tool 28 is too bright, or to brighten the light of the light equipment 3 when being too dark.

Then, with the automatic dimming signal, the aperture driving unit 41 in the light equipment 3 drives the aperture 42 to adjust volume of illumination light which is incident into an incident end of the light guide 14 through the aperture 42 from the lamp 40. With this automatic dimming signal, it is possible to perform the automatic dimming of the brightness near the region where the treatment tool 28 enters in the visual field in the image pickup unit 119 so as to become brightness suitable for observation.

In addition, in this embodiment, the doublet 117*d* which constructs the objective lens system 117 performs control by the auto-focusing unit 137 so that the object image may be always formed on the light-receiving surface of the CCD 118 in a focused state.

In this case, the brightness detection unit 137*a* of the auto-focusing unit 137 detects mean brightness of each frame from a brightness signal from the signal conversion unit 46, and outputs it to the CPU 137C. In addition, the contrast detection unit 137*b* detects contrast in each frame from a brightness signal in a high frequency region in an output signal of the image processing unit 47, and outputs it to the CPU 137C.

The CPU 137C judges whether the brightness detected by the brightness detection unit 137*a* is a predetermined value or larger, and detects a focus condition by a hill-climbing system with the contrast information in the brightness signal in the high frequency region detected by the contrast detection unit 137*b* when exceeding the predetermined value, and it sets the doublet 117*d* at a focused position.

Figure 16:
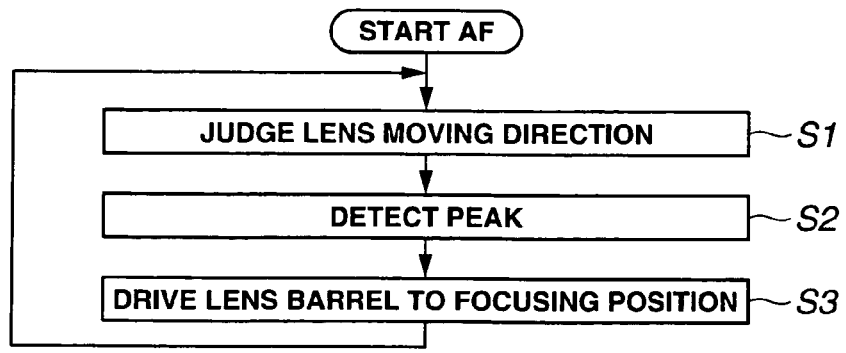
FIG. 16 is a flowchart of an autofocus operation.

FIG. 16 shows contents of processing which performs hill-climbing type auto-focusing (this is written as AF in FIG. 16).

First, at the first step S1, the CPU 137C judges a lens-moving direction. As shown in FIGS. 12 and 13, it performs judgment processing of which direction becomes a hill-climbing direction (direction where contrast becomes large) at a lens position at the start when performing this hill-climbing type auto-focusing.

Specifically, the CPU 137C controls the actuator driving unit 136, moves the doublet 117*d* to one side through the actuator 129, and judges whether the contrast information which is outputted from the contrast detection unit 137*b* becomes large before and after movement at that time. Then, the CPU 137C judges that a direction where contrast becomes large is the lens moving direction to move the doublet 117*d* in the direction.

Then, at the next step S2, the CPU 137C detects a peak value of contrast in the case of moving the doublet 117*d* in the direction where the contrast becomes large. When moving in the mountain climbing direction where contrast becomes large and passing a focusing position (focused position), a contrast value in that case becomes smaller than the peak value.

For this reason, a peak value is detectable by moving the doublet 117*d* to a position of passing over the peak value slightly.

At the next step S3, the CPU 137C controls the actuator driving unit 136 to return the doublet 117*d* to the position corresponding to the peak value. Thus, it is possible to set the doublet 117*d* at the focusing position.

Then, it returns to step S1 and repeats the processing of steps S1 to S3. Thus, it is possible to always keep a focused state and also when a distance to an object changes, it is possible to form an image of the object on the CCD 118 in a high resolution with keeping a predetermined depth of field. Then, an image of the object in the state of being formed on the CCD 118, that is, an image with a high resolution in the state of keeping the predetermined depth of field is shown on the monitor 5. In addition, as explained in a fourth embodiment, when focus control is performed using contrast detected, it is also acceptable to perform control that priority is given to a distant view position over focus control by the contrast, when a brightness level of a brightness signal is small (when it is a dark image).

Next, a case of inserting and dealing with a treatment tool into the channel 25 will be explained. An operator inserts a treatment tool to be used in the treatment tool insert port 27 provided around the operation unit 8. The treatment tool inserted from the treatment tool insert port 27 passes inside the channel 25 of the channel tube 25*a* in the insertion unit 7, and is guided to a side of the distal end portion 11 of the insertion unit 7. When the operator inserts the treatment tool 28 in the deeper side, an end of the treatment tool 28 projects from the channel distal end opening 26 of the distal end portion 11.

Figure 17:
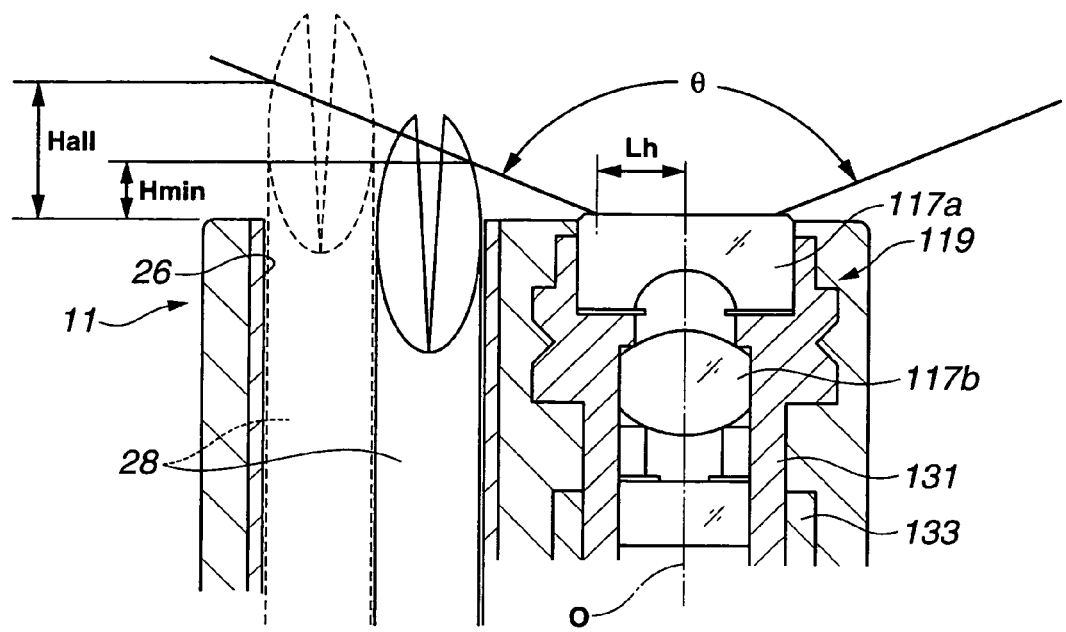
FIG. 17 is a sectional view showing a state in which a treatment tool is inserted into a treatment tool channel and projected from a distal end opening.

With letting a minimum projection amount of the treatment tool 28 from the end surface of the distal end portion 11 of the insertion unit 7 be Hmin, as shown in FIG. 17, when the treatment tool 28 shifts to a nearest side of the image pickup unit 119, a condition necessary for the protruded treatment tool 28 being image-captured by the image pickup unit 119 is deduced, as shown in the following Formula 5 from letting light height Lh on the end lens surface of the image pickup unit 119 be 1.2 mm, letting a radius R of the distal end opening 26 be 1.4 mm, letting an angle θ of view of the image pickup unit 119 be 138°, and letting a distance D between the optical axis O of the image pickup unit 119, and the center of the distal end opening 26 be 6 mm:

$H\min = (D-Lh-R) \times \tan(90° - \phi/2) = 1.38$ mm  (Formula 5)

On the other hand, when the treatment tool 28 is located in a direction of most separating from the image pickup unit 119, a condition necessary for the treatment tool 28 being protruded and the whole end of the treatment tool 28 being image-captured by the image pickup unit 119 is deduced as a projection amount Hall of the treatment tool 28 from the end surface of the distal end portion 11 of the insertion unit 7, as shown in Formula 6:

$H\text{all} = (D-Lh+R) \times \tan(90° - \phi/2) = 2.45$ mm  (Formula 6)

As shown in Formulas 5 and 6, the treatment tool 28 starts to enter in the visual field of the image pickup unit 119 when a protrusion amount from the end surface of the distal end portion 11 becomes at 1.38 mm or more, and almost the whole end of the treatment tool 28 enters in the visual field when being protruded by 2.45 mm.

Thereby, in the state of being set in the near point side of the image pickup unit 119 in this embodiment, a depth of field is set in 5.2 mm to 10 mm, and the end side of the treatment tool 28 enters in the visual field of the image pickup unit 119 securely and becomes visible also on the monitor 5.

Next, with reference to FIG. 18, an operation at the time of picking up an image of an object of a black and white pair of stripes at a 35-μm pitch with the image pickup unit 119 in a state of being set in the near point side will be explained.

Figure 18:
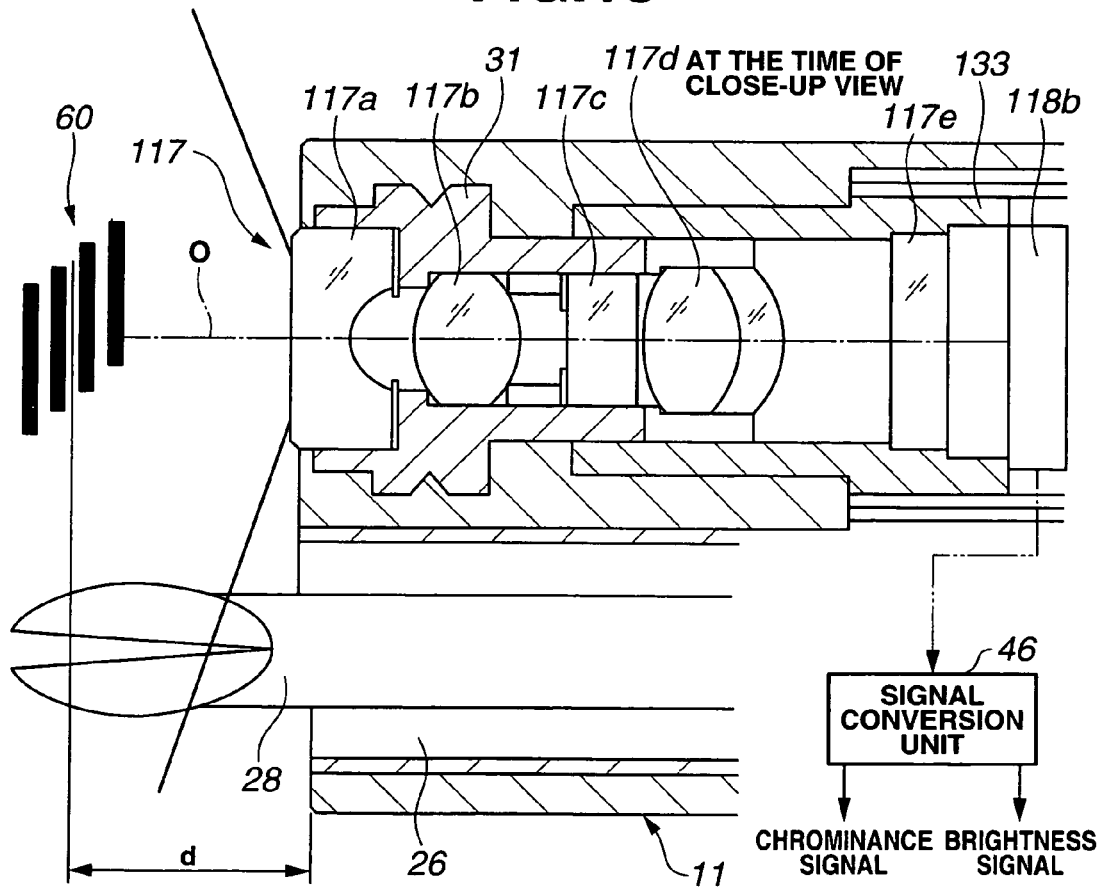
FIG. 18 is a diagram illustrating the effects of the present embodiment on a near point side.

FIG. 18 shows a schematic diagram in the case of inserting the insertion unit 7 of the electronic endoscope 2C of this embodiment into a body cavity, and not only picking up an image of a treatment object region side in the body cavity with the image pickup unit 119 provided in the distal end portion 11, but also protruding the treatment tool 28 from the distal end opening 26 to perform treatment.

In this case, as conditions of facilitating treatment, it is desired not only to be observable in detail for an affected part to be a treatment object, and the like, but also to be observable in detail also for the end side of the treatment tool 28 protruded from the distal end opening 26.

In this embodiment, these are fulfilled as follows. First, in order to clarify explanation more, brightness contrast G (MTF) is defined as follows.

Let a maximum value of brightness by a white object be Gmax and let a minimum value of brightness by a black object be Gmin when an image of the object of black and white stripes with the same width is formed on the light-receiving surface of the CCD 118 with the objective lens system 117, and brightness contrast G=(Gmax−Gmin)/(Gmax+Gmin) is defined.

When the brightness contrast G is defined in this way, in the image pickup unit 119 constructed as mentioned above, when an image of the object of a black and white pair of stripes 60 with a pitch of 35 μm is picked up at the time of an object distances of 5.2 mm to 6.8 mm in a state of being set at the near point, the brightness contrast G of the white stripe and black stripe an image of which is formed on the CCD light-receiving surface becomes 10% or more.

In the image of the object of the black and white pair of stripes at a pitch of 35 μm the image of which is formed on the light-receiving surface of the CCD 118 with the above-mentioned objective lens system 117, difference between an image signal outputted from a pixel on which an image of a white stripe is formed, and an image signal outputted from a pixel on which an image of a black stripe is formed becomes at least almost 10%.

The above-described image signal is inputted into the image processing unit 47 through the CDS circuit 44, A/D converter 45, and signal conversion unit 46, and is given, for example, gamma processing suitable for the monitor 5, and low-pass filtering of removing noise.

Then, with letting a maximum value of a brightness signal obtained from the above-described white object be Imax, and letting a minimum value of a brightness signal obtained from the above-described black object be Imin, contrast I is defined as I=(Imax−Imin)/(Imax+Imin), and in that case, (when an object that a pitch of the above-mentioned black and white pair of stripes is 35 μm is image-captured) it is outputted so that the contrast I may become 10% or more. Thereby, the black and white pair of stripes at a pitch of 35 μm image-captured with the image pickup unit 119 becomes visible as a black and white pair of stripes on the monitor 5. In this way, it becomes observable in a state of being easy to be identified when the contrast I becomes 10% or more.

In FIG. 18, with letting an object distance of 6.8 mm be d in a state of being set in the near point side, a black and white pair of stripes 60 at a 35-μm pitch is arranged at the position, and in that case, photo-electric conversion is performed by the CCD 18, and since, for example, the contrast I in a brightness signal which forms a video signal outputted from the signal conversion unit 46 becomes 10% or more as mentioned above, it becomes possible to visually identify the black and white pair of stripes 60 at a 35-μm pitch on the monitor 5.

Also FIG. 18 shows a state that the treatment tool 28 is protruded from the distal end opening 26 of the channel, and by further protruding it forward after the end of the treatment tool 28 enters into the visual field of the image pickup unit 119, the end of the treatment tool 28 becomes in a state of an object distance d where the black and white pair of stripes 60 at a 35-μm pitch is visible. In this state, since being larger than Hall in Formula 6, the object distance d becomes in a state of satisfying the following condition from Formula 6:

$d \geq (D-Lh+R) \times \tan(90° - \phi/2)$  (Formula 7)

In addition, when rewriting Formula 7, it becomes as follows:

$D \leq d/\tan(90° - \phi/2) + Lh - R$

For this reason, according to this embodiment, in the case of using a varifocal optical system, it is possible not only to observe objects, such as an affected part to be treated with the treatment tool 28, in full detail, but also to observe a state of the end of the treatment tool 28 protruded near it in full detail, and hence, it is easy to perform treatment.

In addition, since the varifocal optical system is used, by changing a focal length of the objective optical system to the distant view side, it is possible to grasp a wide range state to smoothly perform treatment.

This embodiment exhibits the following effects.

In this embodiment, since the varifocal optical system that an angle of view hardly changes when making a focal position variable as the objective lens system 117 which constructs the image pickup unit 119 is adopted, it is possible to obtain an endoscope image in a high resolution from the close-up view side to the distant view side in comparison with the case of a single focal optical system.

Furthermore, since the end side of the treatment tool 28 protruded from the distal end opening 26 of the channel 25 is visible on the monitor 5 in a distance where the black and white pair of stripes at a 35-μm pitch image-captured with the above-described image pickup unit 119 can be visually identified on the monitor 5, it is possible to improve operability due to an angle of view at the time of amplified observation becoming narrow in an endoscope using a conventional zoom optical system. For example, according to this embodiment, it is possible to obtain an effect of becoming easily possible to perform treatment by the treatment tool 28 with performing detailed observation of an object such as a pit pattern of a large intestine.

Moreover, since a distance of a black and white pair of stripes at a 35-μm pitch being visible on the monitor is 5.2 mm to 6.8 mm in the state of being set in the near point side, in this embodiment, it is possible to put the end side of the treatment tool 28 in a visual field in an object distance which is considerably near to this side rather than the distance, and it becomes in a state of reaching a distance, where the highest resolution is obtained, by making it further protruded to the front side.

Hence, in this embodiment, in a distance within the depth of field in a state of being set in the near point side, it is possible to fully put the end side of the treatment tool 28 in a visual field, and it is also possible to obtain an effect that an operation of the treatment tool 28 becomes comparatively easy.

Furthermore, even when it sets in the distant view side, it is possible to keep a predetermined resolution, and to obtain an object image in a state that depth of field is larger than that at the time of the close-up view.

In addition, since auto-focus control is performed so that the varifocal optical system which constructs the objective lens system 117 may be in a focused state, it becomes possible for an operator to observe the endoscope image in a high resolution from the distant view to the close-up view without needing a complicated operation.

Furthermore, since the light equipment 3 controls illumination light volume so that brightness around the treatment tool 28 may become optimum when it becomes in a state that the treatment tool 28 is inserted and its end is shown on the monitor 5, it becomes easy to perform treatment.

In addition, in this embodiment, although it is made that the pixel pitch of CCD118 is 2.5 μm, that effective pixel count is 1,300,000, that a maximum angle of view of the image pickup unit 119 is 138°, that a depth of field in the near point side is 5.2 mm to 10 mm, and that a distance between the optical axis O of the image pickup unit 119, and the center of the distal end opening 26 is 6 mm, it is not limited to these.

For example, even if a pixel pitch, an effectiveness pixel count, a maximum angle of view, and depth of field in a near point side, and the like are changed so that difference between an output signal obtained from a pixel which picks up an image of the above-described white object, and an output signal obtained from a pixel which picks up an image of the above-described black object may become 10% or more when an object where a pitch of a black and white pair of stripes 60 is 35 μm is image-captured, and even if a maximum angle of view, and a distance between the optical axis O of the image pickup unit 119 and the center of the distal end opening 26 in an object distance that the difference between the output signals becomes 10% or more when an image of the above-described 35-μm object is picked up are changed so that the treatment tool may become observable, an almost similar effect is obtained.

In addition, although the effectiveness pixel count of the CCD 118 is 1,300,000 pixels in the above-described explanation, it is possible to obtain similar effects with about 1,500,000 pixels in the case of a mosaic color filter system, and in this case, it is possible to obtain such an effect that it is possible to further enlarge a distance in which a highest resolution can be obtained. Furthermore, although explained using a complementary color-based mosaic filter type color CCD in this embodiment, it is not limited to this, and when a system which uses switching type or other type trichromatic light as illumination light, fetches an object image in a monochrome (black and white) CCD with synchronizing with the trichromatic light which is sequentially radiated, and colorizes it by an image processing apparatus is used in an electronic endoscope, it is possible to obtain a similar effect also in this system by fulfilling the above-mentioned conditions.

In the case of this system, although it is possible to obtain an R signal, a G signal, and a B signal as CCD output signals with an effectiveness pixel count of about 650,000 pixels and it is also possible to output them to the monitor 5 without generating a brightness signal, in this case, what is necessary is just to regard the G signal with the highest brightness as a brightness signal.

In addition, in this embodiment, although highly detailed observation is achieved in the close-up view side by using the actuator as means of moving the doublet 117*d* to change a focal position and performing focal position control by auto-focusing, it is not limited to this, and for example, it is also possible to obtain a similar effect by switching a focal position into the close-up view or distant view by mounting a wire on a shift lever which is provided in the operation unit 8, the wire being mounted on the lens movable frame 134, as means of moving the doublet 117*d*, and operating this shift lever.

As for an angle of view, an angle of view of 100° or more used in a common endoscope in consideration of surrounding observation capability is preferable, and there is such an effect that a wider angle of view makes a treatment tool detection distance shorter.

Furthermore, although the image processing apparatus 4C and the monitor 5 in this embodiment are explained as those corresponding to the HDTV video signal, they are not limited to this, and for example, it is also sufficient to use a display system corresponding to a high-resolution monitor such as SVGA or XGA.

Moreover, in the image pickup unit 119 of this embodiment, although heat radiation to an end portion material of the insertion unit 7 with the heat radiation member 139 and the cable 140 for heat radiation is disclosed as means of radiating heat of the CCD 118, it is also sufficient to adopt such structure that the cable 140 for heat radiation is not provided in the heat radiation member 139, the thermally conductive portion of the end portion material of the insertion unit 7 is made to approach a portion which faces the heat radiation member, and heat is radiated through a thermally conductive sealing resin or the like.

In addition, it is also sufficient to use a part of the signal cable 21 as the cable 140 for heat radiation. For example, it is also sufficient to provide a dummy cable, which is not used for driving, in the signal cable 21, or it is also sufficient to use an outer shield aiming at electromagnetic shielding of the signal cable 21. Furthermore, it is possible to obtain a similar radiating effect by fixing a conductor part of the cable 140 for heat radiation near the CCD chip 118*b* with a conductive sealing resin without providing the heat radiation member 135.

Moreover, it is also effective to suppress heat generation of the CCD chip 118*b* by arranging an output stage inside the CCD chip 118*b* on the CCD substrate 118*c* as an external amplifier to distribute power consumption of the CCD chip 118*b* to parts on the external substrate.

Embodiment 4

Figure 19:
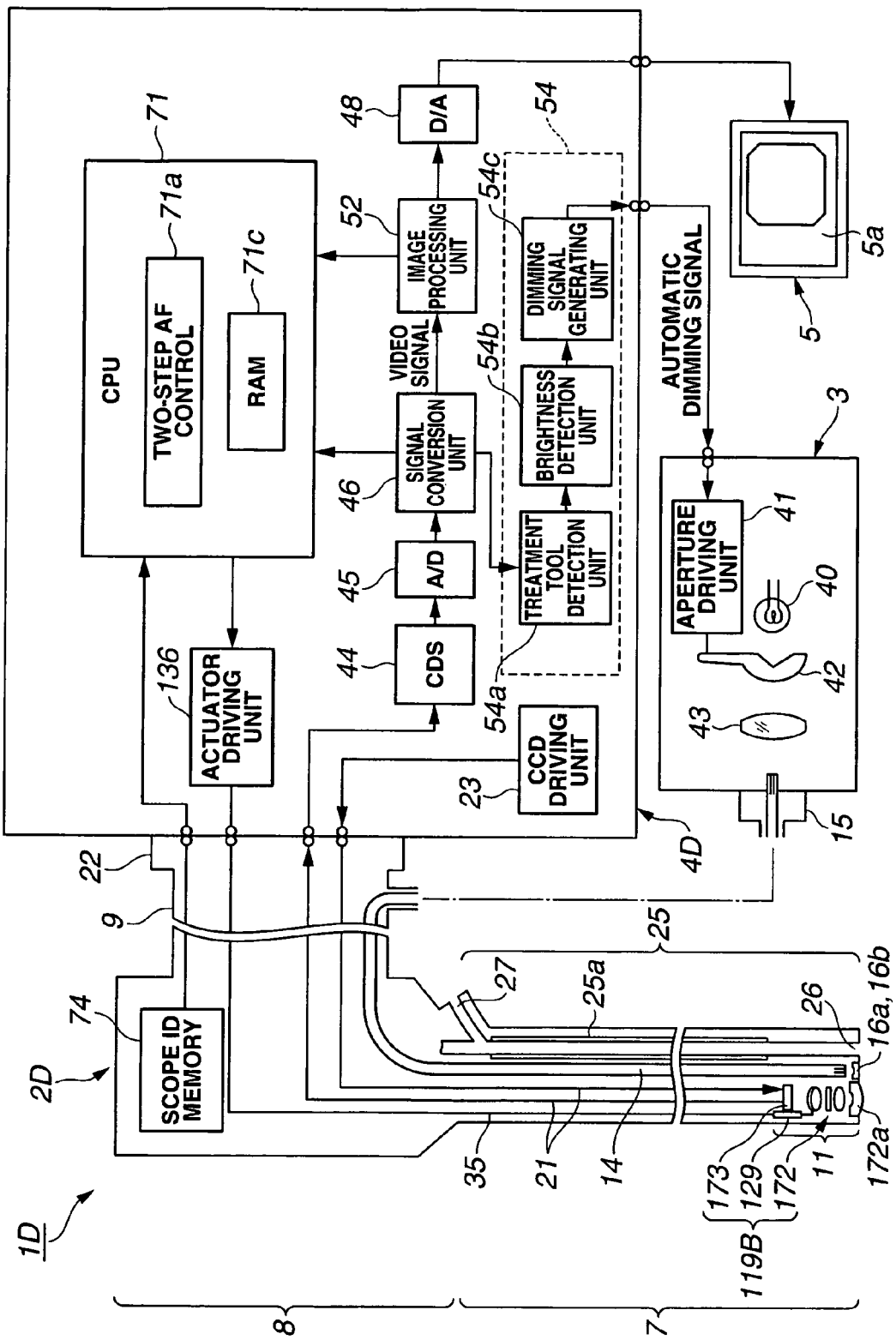
FIG. 19 is a diagram showing the general configuration of an electronic endoscope system comprising Embodiment 4 of the present invention.

Next, a fourth embodiment of the present invention will be described with referring to FIGS. 19 to 23. FIG. 19 shows entire configuration of an electronic endoscope system 1D equipped with a fourth embodiment. This electronic endoscope system 1D comprises an electronic endoscope 2D which is different in a part from the electronic endoscopes 2C in FIG. 11, a video processor 4D equipped with a CPU 71 with a two-step (auto) focus control function 71*a* instead of the auto-focusing unit 137 in the video processor 4C in the third embodiment. In addition, a light source unit 3 and a monitor 5 are the same configuration as those in the third embodiment.

Although fundamental configuration of the electronic endoscope 2D of this embodiment is the same as that of the third embodiment, not only an effectiveness pixel count of the CCD and configurations of a part of an objective lens system are different, but also positional relation between an image pickup unit and a treatment tool channel is different. Hereafter, explanation will be made with emphasis on differences.

Figure 20:
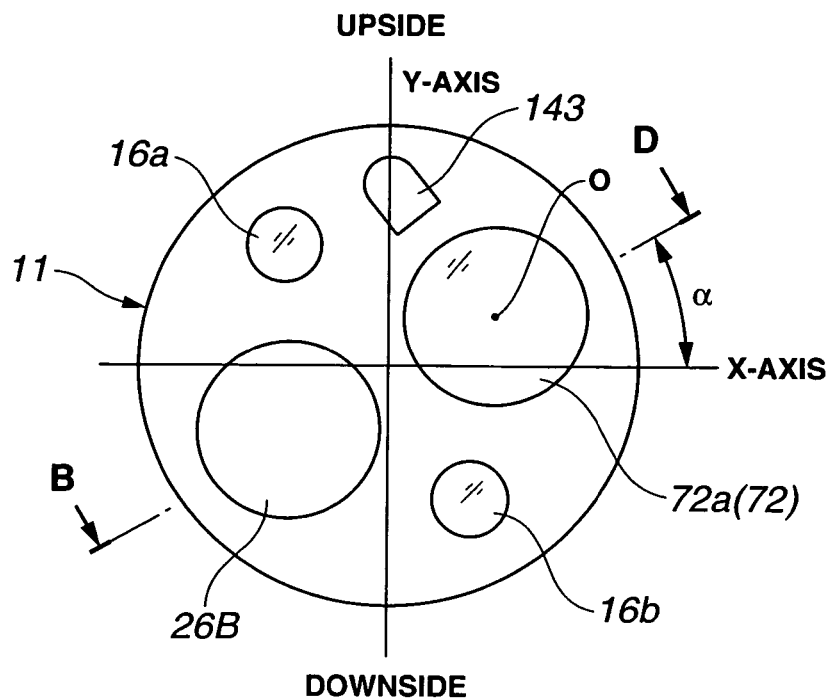
FIG. 20 is a diagram showing the appearance of the distal end surface of the insertion unit distal end according to Embodiment 4 of the present invention as viewed from the front.
Figure 21:
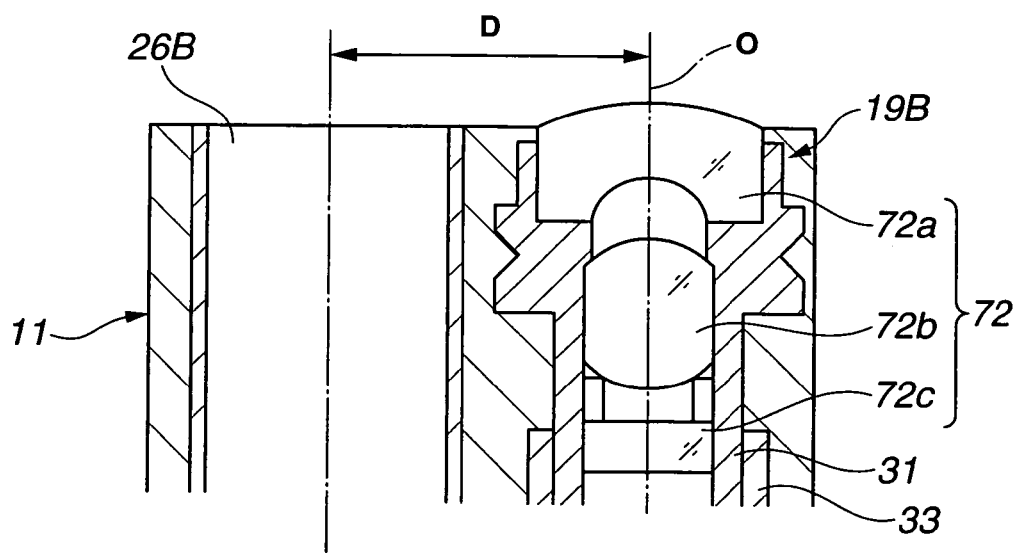
FIG. 21 is a schematic sectional view taken along line D-D in FIG. 17.
Figure 23:
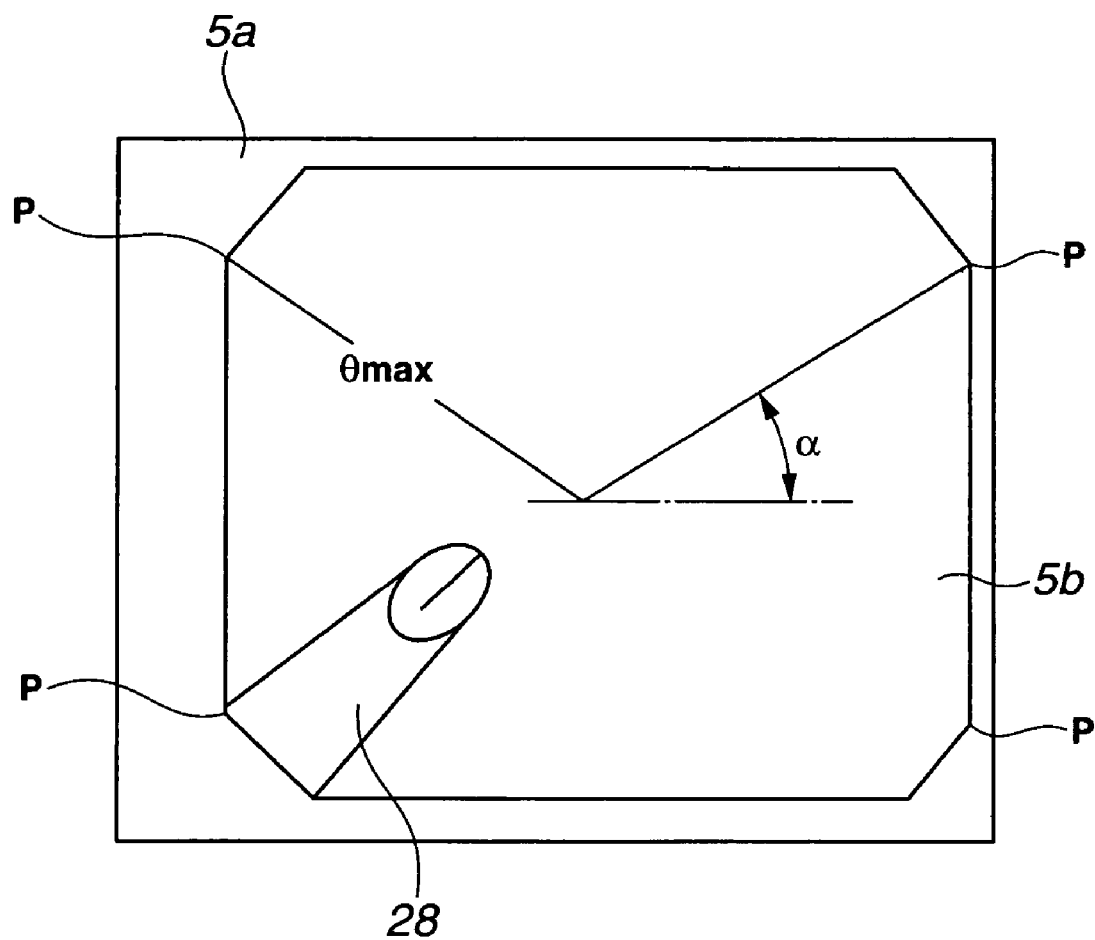
FIG. 23 is a diagram showing a monitor display picture when a treatment tool inserted through a channel according to Embodiment 4 is projected from a distal end.

FIG. 20 is a front view in view of an end surface of an distal end portion 11 of an insertion unit 7 in the electronic endoscope 2D of this embodiment from a front, FIG. 21 is a sectional view taken on line D-D in FIG. 20, and FIG. 23 shows a monitor display image at the time of protruding a treatment tool 28 from the distal end portion 11.

An image pickup unit 119B equipped with an objective lens system 172 and a CCD 173 which is shown in FIG. 20 or 21 is adopted in the distal end portion 11 of the electronic endoscope 2D in this embodiment.

As for this CCD 173, a device that a pixel pitch is 2.8 μm, a pixel count effective for monitor display is 800,000 pixels is adopted.

In addition, the image pickup unit 119B has an objective lens system 172 with a varifocal point that a maximum angle of view becomes 160°, for example, in a state of being set to a near point side (close-up view), and a lens having a meniscus shape is adopted as a first lens 172*a* which is the forefront of this objective lens system 172.

In the distal end portion 11 of the insertion unit 7, as shown in FIG. 20, the image pickup unit 119B which includes the objective lens system 172 that an outer diameter of the first lens 172*a* is φ2.8 mm and a shape is a meniscus, a channel distal end opening 26B, an air-supplying and water-supplying nozzle 143 which supplies water and air to an outer surface of the objective lens system 172 to remove a waste material which adheres to it, and illumination lenses 16*a* and 16*b* for radiating and illuminating an object with light emitted from an end surface of a light guide transmitting illumination light from a light equipment 3 are provided.

The image pickup unit 119B is mounted on an end of an insertion unit so that a vertical direction on the monitor 5 when an image of an object is picked up and is shown on the monitor 5 may coincide with a vertical direction of the end of the insertion unit shown in FIG. 20.

Since a treatment tool channel 25 with an inner diameter of φ2.8 mm is arranged in a left oblique down direction which deviates a little from a horizontal direction, to the image pickup unit 119B, as shown in FIG. 20, with letting a vertical direction of the distal end portion 11 be a Y-axis and letting a crosswise direction be an X-axis, a straight line which connects a central axis of the treatment tool channel 25 and an optical axis O of the image pickup unit 119B forms an angle of α to the above-described X-axis.

As shown in FIG. 21, the optical axis O of the objective lens system 172 and the distal end opening 26B are arranged in parallel, and in this embodiment, a distance D between the center (optical axis O) of the objective lens system 172 and a central axis of the distal end opening 26B is set as 6 mm.

Also in this embodiment, the first lens 172*a*, a second lens 172*b*, and a third lens 172*c* shown in FIG. 21 are mounted on a first lens frame 31, a doublet 117*d* is arranged movably with a lens holding frame 134 similarly to the third embodiment in the CCD frame 133 fitting to this first lens frame 31, and the doublet 117*d* is moved in a direction of the optical axis O through an actuator 129.

In addition, the CPU 71 provided in the video processor 4D moves the doublet 117*d* fundamentally instead of performing auto-focus control continuously in the third embodiment to perform focus control so that a focal position of the objective lens system 172 may become in an approximately focused state between two positions of a close-up view position and a distant view position. Thus, it performs two-step focus control (pseudo one by auto switching).

In this case, the CPU 71 reads ID information of the electronic endoscope 2D connected to the video processor 4D from scope ID memory 74, and stores optical characteristic information of the image pickup unit 119B of this electronic endoscope 2D in a RAM 71C. This optical characteristic information is information with regard to characteristics of a typical contrast change or a resolution at the time when an object distance changes in the case that the doublet 117*d* is set at a position at the time of a close-up view, and the case that it is set at a position at the time of a distant view.

Then, when performing the two-step focus control, the CPU 71 checks temporal responses and others of the contrast information in the state of being set at one position where the doublet 117*d* is actually set, and judges from the change whether it is possible to obtain a larger contrast value by changing it to another position, that is, whether it is closer to a focused state, by referring to the optical characteristic information stored in the RAM 71C.

Then, when judging that it is possible to obtain a larger contrast value by changing it to the another position, the CPU 71 controls an actuator driving unit 136 to set the doublet 117*d* at the another position.

In addition, also when setting the doublet 117*d* at the another position, the CPU 71 monitors the contrast information in the state in time, and performs control so as to make a lens position become nearer to a focused state between two lens positions by performing a similar operation.

In this case, the CPU 71 detects brightness information from a brightness signal from a signal conversion unit 46, further detects contrast information from an image processing unit 47, monitors temporal responses of the contrast information in a state of being in more than predetermined brightness as mentioned above, judges whether it should be switched, by referring to the optical characteristic information, and controls the doublet 117*d* between the two positions according to the decision result. In addition, at the time when predetermined brightness is not obtained, or in an initial state, the CPU 71 performs control of setting it to the distant view position.

In this embodiment, when a switching setup is performed at two positions at the time of a close-up view and at the time of a distant view, the objective lens system 172 in both states shows different optical characteristics, respectively. For example, while it has a highest resolution at the time of the close-up view, it becomes a somewhat low resolution at the time of the distant view in comparison with the time of the close-up view, but it has a larger depth of field than that at the time of the close-up view. Specifically, an F-number is adjusted so that a depth of field may become 4.4 to 12 mm when the doublet 117*d* is set in the close-up view side, and a depth of field may become 9 to 100 mm when it set in the distant view side.

Then, since resolutions in both characteristics have a portion crossed (overlapped) in a state which shows almost reverse tendencies in a middle distance between the close-up view and distant view, it is possible to judge in the cross portion at which position setting of the doublet 117*d* makes a state nearer to a focused state in a state of somewhat deviating from the crossing position. The CPU 71 makes the judgment, and controls position switching of the doublet 117*d* according to the decision result.

In addition, in this embodiment, a depth of field in the objective lens system 172 in a state of being set at the close-up view and that in a state of being set at distant view are set so as to continue (overlap) in a portion not less than a predetermined value, and the contrast I is set so as to overlap in a portion having a predetermined value (for example, 10%) or more in a range to a spatial frequency with a predetermined value.

Next, an operation at the time of the close-up view in this embodiment will be explained.

First, an operation at the time of picking up an image of an object of a black and white pair of stripes at a 35-μm pitch with the image pickup unit 119 in a state of being set at the time of the close-up view will be explained.

In this image pickup unit 119B, when an image of the object of a black and white pair of stripes with a pitch of 35 μm is picked up at the time of an object distance of 4.4 mm to 5.8 mm in a state of being set at the near point, the brightness contrast G of the white stripe and black stripe an image of which is formed on a CCD light-receiving surface becomes 10% or more.

The image of the object of the black and white pair of stripes with a 35-μm pitch which is picked up on the light-receiving surface of the CCD 173 by the above-described objective lens system 172 is given photo-electric conversion. Then, difference between an image signal outputted from a pixel on which the white stripe is image-formed, and an image signal outputted from a pixel on which a black stripe is image-formed becomes 10% or more.

The image signal is inputted into the image processing unit 47 through a CDS circuit 44, A/D converter 45, and signal conversion unit 46 to be given, for example, gamma processing suitable for the monitor, electric mask processing, and the like so as to make the contrast I of the white stripe and black stripe 10% or more, and is outputted to the monitor 5. Since it becomes possible to identify the white stripe and black stripe from the shown image by the contrast I becoming 10% or more in the case of the above-mentioned object, it is possible to observe it in a sufficient resolution. In this manner, according to this embodiment, the black and white pair of stripes at a pitch of 35 μm image-captured with the image pickup unit 119B becomes visible as a black and white pair of stripes on the monitor.

In addition, since a contrast value becomes small when an object distance becomes larger than that at the time of the close-up view, the CPU 71 performs control of switching the doublet 117*d* to the position at the time of the distant view when judging that it is possible to obtain a larger contrast value by the switching.

When switching an observing state to the distant view from the close-up view by performing switching control in this way, it is possible to obtain an endoscope image in a state of being at a lens position nearer to the focused state at two positions.

Figure 22:
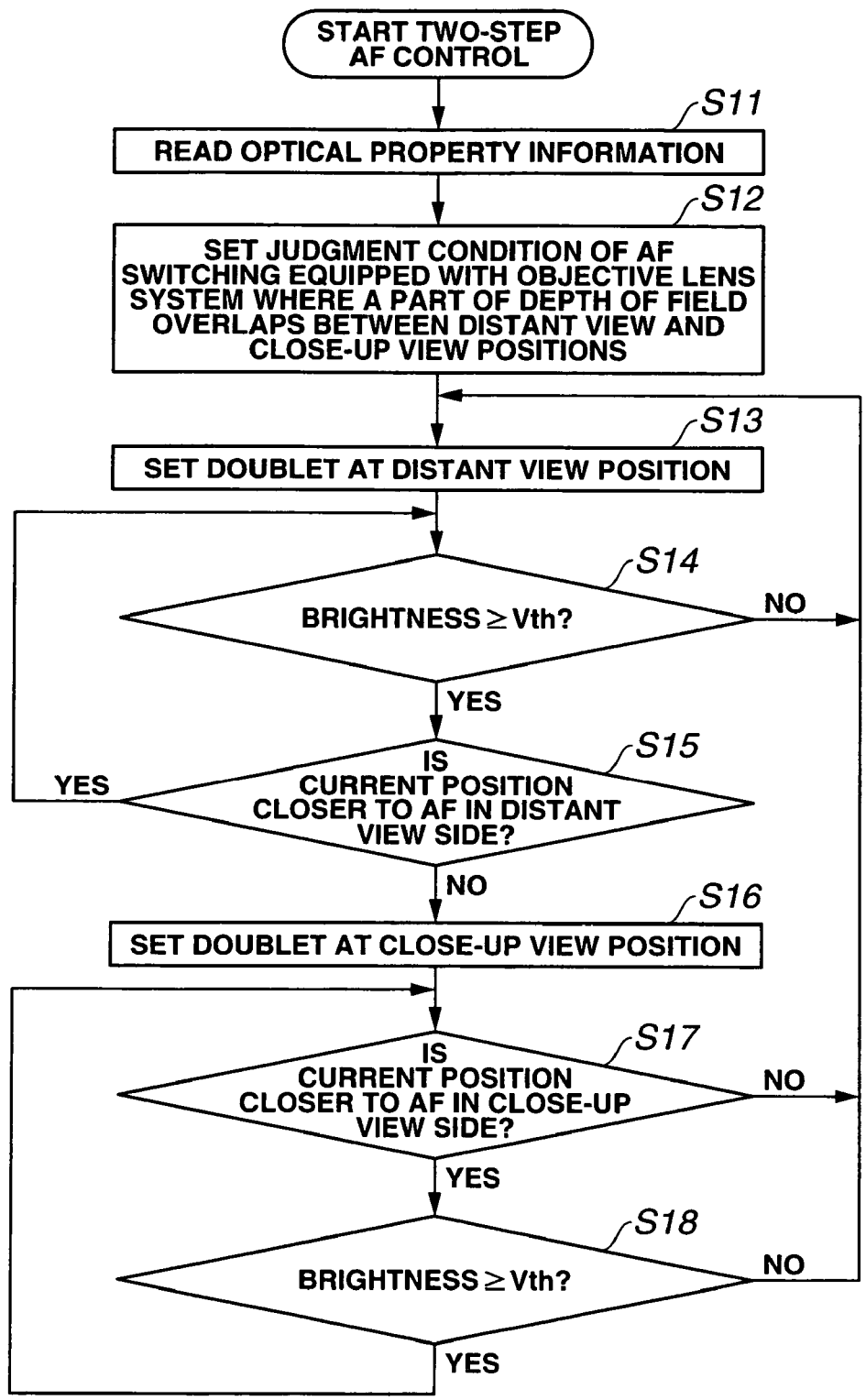
FIG. 22 is a flowchart of a two-step autofocus control operation according to Embodiment 4.

FIG. 22 shows an operation of the two-step auto-focus control (more accurately, two steps approximate auto-focus control) in this embodiment. Hereafter, focusing is abbreviated to AF.

When this operation starts, the CPU 71 reads optical characteristic information from the scope ID memory 74 as initial setting at a first step S11, and stores it in the RAM 71C. In addition, as shown at step S12, the CPU 71 sets the typical contrast information, depth-of-field information, and resolution characteristic information from the optical property information in a state near to AF between the distant view position and close-up view position, as criteria of judgment of AF switching. In addition, when the doublet 117*d* is set at the distant view position and close-up view position, the objective lens system 117 in this embodiment is set so that parts of depths of field in the focused states at respective positions may overlap.

Then, at the next step S13, the CPU 71 performs control processing of setting the doublet 117*d* at the distant view position.

Further, at the next step S14, the CPU 71 judges whether a current brightness level of the brightness signal is not less than a threshold value Vth, which is set beforehand, for judging a dark image state. Then, when judging that it is not more than this threshold value Vth, it returns to step S13 and these processings are repeated with keeping the distant view position. Thus, when proper brightness is not securable even in a state of performing the automatic dimming, the state of being at the distant view position is made to be kept.

It is because of the following reason that, when a brightness level of the brightness signal is not more than the threshold Vth, the doublet 117*d* is set at the distant view position. Since the insertion unit 7 of the electronic endoscope 2D is inserted into a body cavity, illumination light is emitted from the illumination lenses 16*a* and 16*b* provided in the end surface of the distal end portion 11, and an object such as an affected part is illuminated, lack of illumination light volume hardly arises when a distance to the object is small. For this reason, when the brightness level of the brightness signal is not more than the threshold Vth, it is considerable that there is the object far away. In addition, since an S/N ratio drops when a brightness level of a brightness signal is not more than the threshold Vth, high-precision focus control becomes difficult. For such a reason, when a brightness level of a brightness signal is not more than the threshold Vth, the doublet 117*d* is set at the distant view position.

On the other hand, when judging that it is not less than the threshold Vth, at step S15, the CPU 71 judges whether the contrast value presently detected is nearer to the case in the distant view side (than the close-up view side), using the criteria of judgment.

Then, in the case of fulfilling this condition, it returns to step S14, and these processings are repeatedly performed. In the case of not fulfilling the condition at step S15, as shown at step S16, the CPU 71 performs control processing of setting the doublet 117*d* at the close-up view position.

Then, at step S17, the CPU 71 judges whether the contrast value presently detected is nearer to the case in the close-up view side (than the distant view side). In the case of not fulfilling this condition, it returns to step S13 and performs the processing of setting it at the distant view position.

On the other hand, in the case of fulfilling this condition, as shown at step S18, the CPU 71 judges whether a current brightness level of the brightness signal is not less than the threshold value Vth, which is set beforehand, for judging a dark image state. Then, when judging that it is not more than this threshold value Vth, it returns to step S13. On the contrary, when judging that it is not less than the threshold value Vth, it returns to step S17.

When switching an observing state to the distant view from the close-up view by performing the two-step AF control in this way, it is possible to obtain an endoscope image in a state of being at a lens position nearer to the focused state at two positions.

In addition, electric mask processing creates an octagonal display area 5b with an aspect ratio of 1:1.2 in the display screen of the monitor 5 as shown in FIG. 23, and makes an object image-captured with the image pickup unit 119B displayed in the octagonal display area 5b.

In the case of an oblong display area as shown in FIG. 23, as for an angle of view on the display area 5b obtained by above-described electric mask processing, a point P in a diagonal direction becomes a largest angle of view (θmax). The mask processing is performed so that 160° of angle of view of the objective lens system 172 may coincide with the above-described maximum angle θmax of view. On the other hand, by the mask processing, what an angle of view becomes narrowest on the monitor screen is a vertical direction, and, secondly an angle of view in a crosswise direction becomes narrow.

Furthermore, the point P to become the above-described maximum diagonal is set so that an angle formed by a straight line which connects the point P and a screen center, and a horizontal direction on the monitor screen may be set at α, and further, the image pickup unit 119B is arranged so that an X-axis direction of the distal end portion 11 of the insertion unit and the monitor horizontal direction may coincide as shown in FIG. 20, and hence, the treatment tool 28 protruded from the distal end opening 26B of the treatment tool channel 25 arranged in a position becoming the angle α to the X-axis is displayed as shown in FIG. 23 within the display area 5b from an approximately horizontal direction on the monitor 5, or more strictly, from a lower left point P which is a little lower than the horizontal direction.

With letting a minimum projection amount of the treatment tool 28 from the end surface of the distal end portion 11 be Hmin, when the treatment tool 28 shifts most nearly to a side of the image pickup unit 119B, a condition necessary for the treatment tool 28 being image-captured by the image pickup unit 119B, the treatment tool 28 protruded from the distal end opening 26B of the distal end portion 11 of the insertion unit is deduced, as shown in the following Formula 8 from letting light height Lh on the end lens surface of the image pickup unit 119B be 1.31 mm, letting a radius R of the distal end opening 26B be 2.8 mm, letting an angle θ of view of the image pickup unit 119B be 160°, and letting a distance D between the optical axis O of the image pickup unit 119B, and the channel 25 be 6 mm:

$$H\text{min}=(D-Lh-R)\times\tan(90°-\theta/2)=0.58 \text{ mm} \quad \text{(Formula 8)}$$

On the other hand, when the treatment tool 28 is located in a direction of most separating from the image pickup unit 119B, a condition necessary for the treatment tool 28 being protruded and a whole end of the treatment tool 28 being image-captured by the image pickup unit 119B is deduced as a projection amount Hall of the treatment tool 28 from the end surface of the distal end portion 11, as shown in Formula 9:

$$H\text{all}=(D-Lh+R)\times\tan(90°-\phi/2)=1.07 \text{ mm} \quad \text{(Formula 9)}$$

As shown in Formulas 8 and 9, the treatment tool 28 starts to enter in the visual field of the image pickup unit 119B when a protrusion amount from the end surface of the distal end portion 11 becomes at 0.58 mm or more, and almost the whole end of the treatment tool 28 enters in the visual field when being protruded by 1.07 mm.

Thereby, within a distance of 4.4 mm to 5.8 mm, where the black and white pair of stripes at a 35-μm pitch is visible on the monitor, in the state of being set in the near point side of the image pickup unit 119B in this embodiment, the end side of the treatment tool 28 enters in the visual field of the image pickup unit 119B and becomes visible also on the monitor 5.

This embodiment exhibits the following effects.

In this embodiment, since the varifocal optical system that a focal distance changes is adopted as the objective optical system which constructs the image pickup unit 119B, it is possible to obtain an image with a higher resolution from the close-up view side to the distant view side than the case of a single focal optical system.

Here, in this embodiment, although it is made that the pixel pitch of CCD 173 is 2.8 μm, that effective pixel count is 800,000, that a maximum angle of view of the image pickup unit 119B is 160°, that depth of field in the state of being set in the near point side is 4.4 mm to 12 mm, and that the distance between the optical axis O of the image pickup unit 119B, and the center of the distal end opening 26 is 6 mm, it is not limited to these.

For example, even if a pixel pitch, an effectiveness pixel count, a maximum angle of view, and depth of field in a near point side, and the like are changed so that difference between an output signal obtained from a pixel which picks up an image of the above-described white object, and an output signal obtained from a pixel which picks up an image of the above-described black object may become 10% or more when an object where a pitch of a black and white pair of stripes is 35 μm is image-captured, and even if a maximum angle of view, and a distance between the optical axis O of the image pickup unit 19 and the center of the distal end opening 26 in an object distance that the difference between the output signals becomes 10% or more when an image of the above-described 35-μm object is picked up are changed so that the treatment tool may become observable, an almost similar effect is obtained.

In addition, although the effectiveness pixel count is 800,000 pixels in this embodiment, it is possible to obtain similar effects with about 600,000 pixels in the case of the mosaic color filter system, and in this case, since the depth of field in the near point side is enlarged to spread the cross region in depth with the depth of field in the far point side, it is possible to obtain such an effect that it is possible to make focal switching more smooth.

Furthermore, also in this embodiment, it is possible to adopt a system which uses switching type or other type trichromatic light as illumination light, fetches an object image in a monochrome (black and white) CCD with synchronizing with the trichromatic light which is sequentially radiated, and colorizes it by an image processing apparatus, and in this case, when a CCD with an effective pixel count of about 250,000 pixels is used, it is possible to obtain effects equivalent to those of mosaic filter type 600,000-pixels.

In addition, in this embodiment, although the display area 5b of the monitor screen 5a is made an oblong octagon where horizontal display size is longer than that in a vertical direction (longitudinal direction) as shown in FIG. 23, it is not limited to this case.

Moreover, more generally, it is also sufficient to make the treatment tool 28, protruded from a distal end opening, displayed in a direction where display area is wider by arranging this distal end opening so as to correspond in the direction where the display area is wider (or larger) in the display area. The "direction where a display area is wider" here means a direction where restriction of a display area of an observed image displayed on a screen is few (or there is no restriction) in comparison with other directions because of electronic mask processing and the like.

Figure 24:
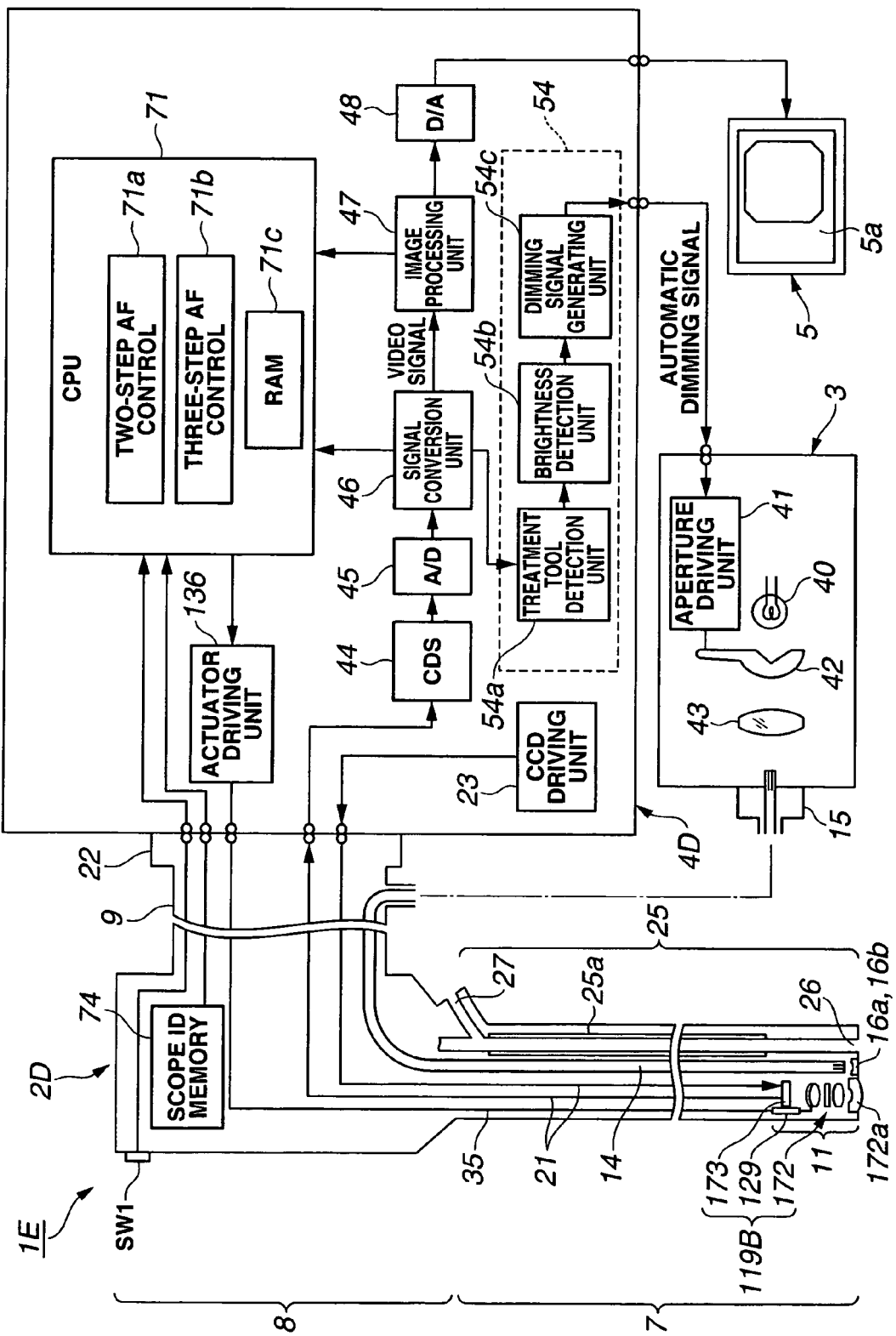
FIG. 24 is a diagram showing the general configuration of an electronic endoscope system according to a first variation of Embodiment 4.

In addition, as a first modified example of this embodiment, as shown in FIG. 24, it is also sufficient to make it possible to select the two-step auto-focus control function 71a or a three-step auto-focus control function 71b with a mode changeover switch SW1 by means of the CPU 71.

In an electronic endoscope system 1E shown in FIG. 24, the CPU 71 has the three-step auto-focus control function 71b besides the two-step auto-focus control function 71a in, for example, the electronic endoscope system 1D of FIG. 19.

Then, this CPU 71 performs focus control in a two-step auto-focusing mode or a three-step auto-focusing mode according to a selection signal selected by the mode changeover switch SW1 provided, for example, in the operation unit 8 of the electronic endoscope 2D.

Also in this modified example, optical characteristic information unique in the electronic endoscope 2D is stored in the scope ID memory (memory) 74. In this case, the optical characteristic information with regard to the contrast values and the like at the time of setting the doublet 117d at a midpoint set between the near point and far point besides the near point and far point is stored. In addition, information of driving (moving) the doublet 117d at the position of the midpoint is also stored.

Then, the CPU 71 of the video processor 4D reads the optical characteristic information to store it in, for example, the RAM 71C, and performs the two-step focus control or three-step focus control in the fourth embodiment.

As a merit of performing the three-step focus control, since the vicinity of the midpoint of both points becomes a valley of both optical characteristics in the two-step focus control using the near point and far point, it is apt to become difficult to improve, for example, a depth of field and a resolution so as to have more preferable characteristics.

For example, when depths of field are continuously not less than a predetermined value at the time of the close-up view and distant view and are switched also to a position of a midpoint of both points to the case that the contrast I is 10% or more, it becomes possible to make it continue with values of the depth of field and values of the contrast I which are larger than these conditions to achieve the optical characteristics further improved.

In this way, by adopting a configuration which can set the doublet 117d also to the position of the midpoint between the near point and far point, it becomes possible to further enlarge a depth of field and a resolution, and hence, it is possible easily to achieve more preferable optical characteristics.

A control method of performing the three-step focus control is similar to that of the two-step. For example, in a state of setting it at the near point, the CPU 71 monitors temporal responses of the contrast information in the state, and judges whether switching between the state of the near point and the midpoint, in that case. In addition, also in the state of being set at the midpoint, it monitors the temporal responses of the contrast information and judges which of the near point side and far point side is suitable as a switched side according to a changing direction to the near point side, or to the far point side. For this reason, it is also possible to perform the three-step focus control by the control similar to the case of the fourth embodiment.

Figure 25:
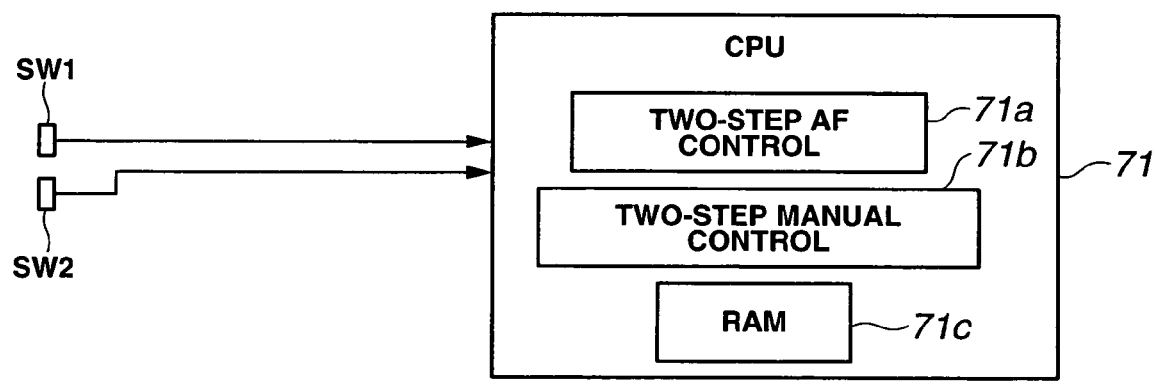
FIG. 25 is a diagram showing the configuration of a CPU portion in a second variation of Embodiment 4.

FIG. 25 shows a portion of the CPU 71 in a second modified example. As shown in FIG. 25, for example, it is also sufficient that the CPU 71 performs the two-step auto-focus control function 71a or the two-step manual control function 71d according to a mode switching instruction signal of the mode changeover switch SW1.

The two-step auto-focus control function 71a is the same as what is explained in the fourth embodiment. When it is set in the two-step manual control mode with the mode changeover switch, the CPU 71 moves the doublet 17d to the near point side when a near point instruction switch in the manual operation switch SW2 is operated.

On the other hand, when a far point instruction switch in the manual operation switch SW2 is operated, the CPU 71 performs the control operation of moving the doublet 117d to the far point side.

In this way, by providing mode selection means, the choice of observation (image pickup) in the case of performing a diagnosis and the like using the electronic endoscope 2D (image sensing) becomes wide for an operator, and it is possible to achieve what is easier to use.

Although explanation of performing the two-step auto-focus control function 71a and the two-step manual control function 71d is given in FIG. 25, it is also sufficient to perform the three-step auto-focus control function 71b and a three-step manual control function. In addition, it is also sufficient to perform two or more steps of auto-focus control function, and two or more steps of manual control function using a CPU or the like.

Furthermore, it is also sufficient to perform continuous auto-focus control, two or more steps of focus control, and continuation or two or more steps of manual control using a CPU or the like according to a mode switching instructing operation.

Moreover, although the image processing apparatus 4D and the monitor 5 in this embodiment are explained as those corresponding to the HDTV video signal, they are not limited to this, but, it is also sufficient to use, for example, what corresponds to an NTSC or PAL video signal. In addition, it is also sufficient to use what conforms to a VGA system or an SVGA system.

In addition, embodiments constructed by partially modifying or combining the embodiments mentioned above belong to the present invention.

What is claimed is:

1. An electronic endoscope comprising:
    an insertion unit that is inserted into a subject;
    a channel formed in the insertion unit and through which a treatment tool can be inserted;
    a single-focus objective optical system provided at a distal end of the insertion unit to form an optical image of the subject; and
    an image capturing element having a light receiving surface placed at a position where the objective optical system forms an image, to execute a photoelectric conversion on the optical image formed on the light receiving surface,
    wherein an image of a subject comprising a black band and a white band which have the same width is captured via the objective optical system and a brightness signal is generated from the resulting image signal and a maximum value of a brightness signal for the white subject is defined as Imax, a minimum value of a brightness signal for the black subject is defined as Imin, and a contrast I is defined by I=(Imax−Imin)/(Imax+Imin), and wherein the objective optical system and the channel are formed such that:
    an image signal is output such that the contrast I defined above is at least almost 10%, the contrast I being obtained by capturing an image of a subject comprising a 0.5-mm pitch black and white band pair at a first object distance of 50 mm from the distal end of the insertion unit, and at a second object distance shorter than the first object distance at which an image signal is output such that the contrast I defined as described above is at least almost 10%, the contrast I being obtained by capturing an image of a subject comprising a 35-μm pitch black and white band pair, an image of vicinity of the distal end of the treatment tool projected from a distal end opening in the channel is formed on the light receiving surface of the image capturing element.

2. The electronic endoscope according to claim 1, wherein an image capturing device including the objective optical system and the image capturing element has a view angle of at least 100°, and the image capturing element has a mosaic color filter for which the number of pixels effective for monitor display is at least 250 thousand and at most 850 thousand.

3. The electronic endoscope according to claim 1, wherein if a height of light on a distal end surface of the objective optical system is defined as Lh, the radius of the distal end opening of the channel is defined as R, a distance between an optical axis of the objective optical system and the center of the distal end opening is defined as D, an angle of view at which an image can be formed in the image capturing element via the objective optical system is defined as θ, and an amount of projection of the treatment tool from the distal end of the insertion unit is defined as Hall, when the object distance is defined as d, the following equation is satisfied:

$$\text{Hall}=(D-Lh+R)\times\tan(90°-\theta/2)\leq d.$$

4. An electronic endoscope system comprising:

an electronic endoscope having an insertion unit including a channel through which a treatment tool can be inserted, a single-focus objective optical system that forms an optical image of a subject, and an image capturing element having a light receiving surface placed at a position where the objective optical system forms an image, which photoelectrically converts the optical image formed on the light receiving surface, and an image processing device that converts an image signal from the image capturing element into a video signal, wherein an image of a subject comprising a black band and a white band which have the same width is captured via the objective optical system and the image processing device generates, from an image signal obtained, a video signal that can be displayed on a monitor, a maximum value of a brightness signal for the white subject is defined as Imax, a minimum value of a brightness signal for the black subject is defined as Imin, and a contrast I is defined by I=(Imax−Imin)/(Imax+Imin), the objective optical system and the channel are formed such that:

an image signal is output such that the contrast I defined above is at least almost 10%, the contrast I being obtained by capturing an image of a subject comprising a 0.5-mm pitch black and white band pair at a first object distance of 50 mm from the distal end of the insertion unit, and at a second object distance shorter than the first object distance at which an image signal is output such that the contrast I defined as described above is at least almost 10%, the contrast I being obtained by capturing an image of a subject comprising a 35-μm pitch black and white band pair, an image of vicinity of the distal end of the treatment tool projected from a distal end opening in the channel is displayed on the monitor.

5. The electronic endoscope system according to claim 4, wherein when a display area on the monitor has different lengths in a vertical direction and a horizontal direction the distal end opening of the channel is located in association with the direction in a display area on the monitor in which the length is longer the display area showing an optical image captured by the image capturing element.

6. The electronic endoscope system according to claim 4, further comprising:

a light source that generates illumination light with which the subject is illuminated;

a treatment tool detection unit that detects that the treatment tool projecting from the distal end opening of the channel is to be displayed on the monitor, based on the image signal output from the image capturing element;

a brightness detection unit that detects the brightness of the image signal of the vicinity of the treatment tool displayed on the monitor; and a light quantity adjusting unit that adjusts the quantity of illumination light with which the subject is irradiated on the basis of detection result by the brightness detection unit.

7. The electronic endoscope system according to claim 4, wherein an image capturing device including the objective optical system and the image capturing element has a view angle of at least 100°, and the image capturing element has a mosaic color filter for which the number of pixels effective for monitor display is at least 250 thousand and at most 850 thousand.

8. The electronic endoscope system according to claim 4, wherein if a height of light on a distal end surface of the objective optical system is defined as Lh, the radius of the distal end opening of the channel is defined as R, a distance between an optical axis of the objective optical system and the center of the distal end opening is defined as D, an angle of view at which an image can be formed in the image capturing element via the objective optical system is defined as θ, and an amount of projection of the treatment tool from the distal end of the insertion unit is defined as Hall, when the object distance is defined as d, the following equation is satisfied:

$$\text{Hall}=(D-Lh+R)\times\tan(90°-\theta/2)\leq d.$$

* * * * *